US009701629B2

(12) United States Patent
Nothofer et al.

(10) Patent No.: US 9,701,629 B2
(45) **Date of Patent: *Jul. 11, 2017**

(54) USE OF DITHIOCARBAMATE ESTERS AND BIS-DITHIOCARBAMATE ESTERS IN THE PREPARATION OF ORGANIC-INORGANIC NANOCOMPOSITES

(75) Inventors: Heinz-Georg Nothofer, Stuttgart (DE); Jurina Wessels, Stuttgart (DE); William E. Ford, Stuttgart (DE); Akio Yasuda, Esslingen (DE)

(73) Assignee: SONY DEUTSCHLAND GmbH, Berlin (DE)

( * ) Notice: Subject to any disclaimer, the term of this patent is extended or adjusted under 35 U.S.C. 154(b) by 461 days.

This patent is subject to a terminal disclaimer.

(21) Appl. No.: 11/324,416

(22) Filed: Jan. 3, 2006

(65) Prior Publication Data

US 2006/0163564 A1 Jul. 27, 2006

Related U.S. Application Data

(63) Continuation-in-part of application No. 10/006,636, filed on Dec. 6, 2001, now Pat. No. 7,030,271.

(30) Foreign Application Priority Data

Dec. 8, 2000 (EP) .................................... 00126968

(51) Int. Cl.

| | |
|---|---|
| ***B82Y 10/00*** | (2011.01) |
| ***C07C 323/60*** | (2006.01) |
| ***B82Y 30/00*** | (2011.01) |
| ***C07C 321/04*** | (2006.01) |
| ***C07C 333/14*** | (2006.01) |
| ***H01B 1/12*** | (2006.01) |
| ***H01L 51/00*** | (2006.01) |
| ***H01L 51/05*** | (2006.01) |
| ***C40B 40/02*** | (2006.01) |

(52) U.S. Cl.

CPC ............ *C07C 323/60* (2013.01); *B82Y 10/00* (2013.01); *B82Y 30/00* (2013.01); *C07C 321/04* (2013.01); *C07C 333/14* (2013.01); *C40B 40/02* (2013.01); *H01B 1/121* (2013.01); *H01L 51/005* (2013.01); *H01L 51/0595* (2013.01); *H01L 51/0052* (2013.01)

(58) Field of Classification Search

None

See application file for complete search history.

(56) References Cited

U.S. PATENT DOCUMENTS

| | | | | |
|---|---|---|---|---|
| 2,735,267 | A * | 2/1956 | Walton | 60/362 |
| 3,915,962 | A | 10/1975 | Brand et al. | |
| 4,394,439 | A * | 7/1983 | Robillard | 430/336 |
| 6,984,265 | B1 * | 1/2006 | Raguse et al. | 117/73 |
| 7,211,439 | B2 * | 5/2007 | Vossmeyer | 436/151 |

FOREIGN PATENT DOCUMENTS

| | | |
|---|---|---|
| DE | 11 34 063 | 8/1962 |
| JP | 50142174 | 11/1976 |
| WO | WO 96 07487 | 3/1996 |

OTHER PUBLICATIONS

Huttner et al (1971 Angew Chem international Ed. 10: 556-7).*
Brousseau et al (1999 Advanced Materials 11:447-9).*
Sulfur electtronegativity downlowded from webelements.com Jul. 29, 2016.*
Carbon electtronegativity downlowded from webelements.com Jul. 29, 2016.*
U.S. Appl. No. 11/360,298, filed Feb. 23, 2006, Wessels, et al.
R.N. Misra et al.., "The Use of Some Thioglycollanilides in Inorganic Analysis", Journal of the Indian Chemical Society, vol. 32, pp. 127-134, (1955).
A.S. Aswar et al., "Strucutural and Conducting Studies on Manganese- , Cobalt-, Nickel-, Copper-, Zinc- and Cadmium (II) Polychelates", Journal of the Indian Chemical Society, vol. 74, No. 9, Sep. 1997, pp. 679-682.
I.M. Sarin et al., "Preparation and Characterisation of Some New Polymeric Chelates of Transition Metal Ions", Asian Journal of Chemistry, vol. 10, No. 2, 1998, pp. 221-227.
E.B. Knott, "Heterocyclyl-Rhodamines and -2-thiohydantoins", Journal of the Chemical Society, 1956, pp. 1644-1669.
E. Cullen et al., "Bis Basic Substituted Diaminobenzobisthiazoles as Potential Antiarthritic Agents", Journal of Medicinal Chemistry, vol. 35, No. 2, Jan. 24, 1992, pp. 350-361.
V.N. Elokhina et al., "Reaction of Acylacetylenes and Methyl Propiolate with N, N'- bis(dithiocarboxy)piperazine", Bulletin of the Academy of Sciences of the USSR, Division of Chemical Science, vol. 39, No. 11, pt. 2, Nov. 1990, pp. 2390-2393.
N.G. Lukyaneko et al., "Macroheterocycles; XX. Synthesis of Cryptands Containing Urea and Thiourea Moieties", Synthesis, No. 2, Feb. 1984, p. 137.
N. Uehara et al., "Spectrophotometric Studies for Complex Formulation of Diammonium 1, 4, 10, 13-tetraoxa-7, 16-diazacyclooctadecane-bis(N-thioate) with transitional metal ions under coexistence of alkali metal ion and alkaline earth metal ion", Chemistry Letters, No. 7, Jul. 1999, pp. 709-710.

(Continued)

*Primary Examiner* — Christopher M Gross
(74) *Attorney, Agent, or Firm* — Oblon, McClelland, Maier & Neustadt, L.L.P.

(57) ABSTRACT

The invention relates to tuned multifunctional linker molecules for charge transport through organic-inorganic composite structures. The problem underlying the present invention is to provide multifunctional linker molecules for tuning the conductivity in nanoparticle-linker assemblies which can be used in the formation of electronic networks and circuits and thin films of nanoparticles. The problem is solved according to the invention by providing a multifunctional linker molecule of the general structure $$CON_1\text{-}FUNC_1\text{-}X\text{-}FUNC_2\text{-}CON_2$$

in which X is the central body of the molecule, $FUNC_1$ and $FUNC_2$ independently of each other are molecular groups introducing a dipole moment and/or capable of forming intermolecular and/or intramolecular hydrogen bonding networks, and $CON_1$ and $CON_2$ independently of each other are molecular groups binding to nanostructured units comprising metal and semiconductor materials.

20 Claims, 8 Drawing Sheets

(56) References Cited

OTHER PUBLICATIONS

M. Brust et al., "Novel Gold-Dithiol Nano-Networks with Non-Metallic Electronic Properties", Advanced Materials, vol. 7, No. 9, Sep. 1995, pp. 795-797.
U.S. Appl. No. 13/620,847, filed Sep. 15, 2012.

* cited by examiner

Figure 1
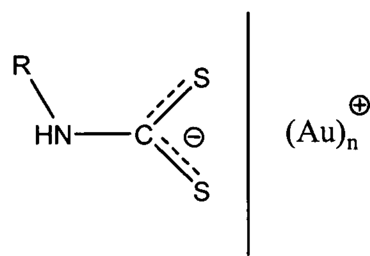
Figure 1a
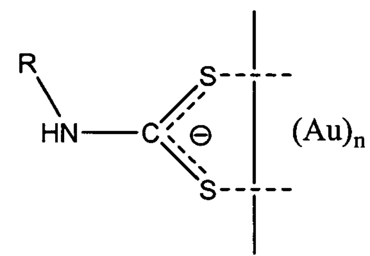
Figure 1b
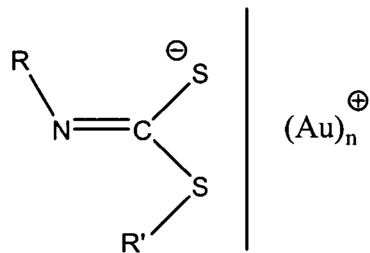
Figure 1c
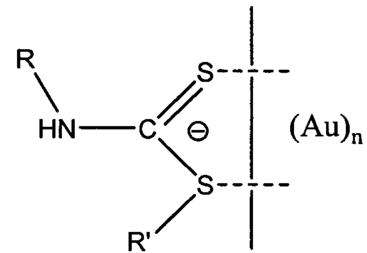
Figure 1d

USE OF DITHIOCARBAMATE ESTERS AND BIS-DITHIOCARBAMATE ESTERS IN THE PREPARATION OF ORGANIC-INORGANIC NANOCOMPOSITES

This application is a continuation-in-part application of the co-pending application Ser. No. 10/006,636, filed Jun. 12, 2001. For the purposes of the present invention, all references as cited are herewith incorporated by reference in their entireties.

DESCRIPTION

The invention relates to multifunctional linker molecules for tuned charge transport through organic-inorganic composite structures and assemblies and nanoelectronic devices comprising such multifunctional linker molecules. The invention further relates to the use of such multifunctional linker molecules. This invention furthermore relates to the significant superiority of dithiocarbamate esters over the use of dithiocarbamate salts as interlinking molecules in the self-assembly process for the above organic-inorganic composite structures and assemblies and nanoelectronic devices.

One-dimensional, two-dimensional, and three-dimensional arrays of nanometer-sized particles coupled by multifunctional linkers have potential applications in nanometer sized computational or memory devices. A key enabling technology for designing such nanoelectronic devices is the ability to tune the conductivity in such assemblies by altering the structure of the linker molecules.

The multifunctional linker molecules connect the nanostructured units with each other through tunnel barriers. It has been shown in the literature that charge transport via through-bond tunneling is a major channel for charge transport (Slowinskli, K., Chamberlain, R. V., Miller, C. J., Majda, M. (1997) J. Am. Chem. Soc. 119, 11910-11919 "Through-bond and chain-to-chain coupling. Two pathway electron tunneling through liquid alkanethiol monolayers on mercury electrodes").

It has been suggested that the orbital overlap between the nanostructured unit and the binding group of the linker molecule is an important factor in charge transport through these assemblies (Bakkers, E. P. A. M., Marsmann, A. W., Jenneskens, L. M., Vanmaekelbergh, D. (2000) Angew. Chemie 112, 2385-2388 "Abstandsabhängiger Elektronentransfer in Au/Spacer/Q-CdSe-Anordnungen"). Thus, the design of the linker molecules and in particular the connecting group provides a means of tuning the conductivity through these assemblies. The electrical properties of various 1-dimensional, 2-dimensional, and 3-dimensional assemblies of nanostructured units have been described in the literature. In 2-dimensional superlattice arrays of Au-nanoparticles molecularly linked by aryl di-isonitriles, both nonlinear Coulomb-charging behavior as well as Ohmic behaviour has been reported in the literature (Janes, D. B., Kolaguta, V. R., Osifchin, R. G., Bielefeld, J. D., Andres, R. P., Henderson, J. I., Kubiak, C. P. (1995) Superlattices and Microstructures 18, 275-282 "Electronic conduction through 2D arrays of nanometer diameter metal clusters", Andres, R. P., Bielefeld, J. D., Henderson, J. I., Janes, D. B., Kolagunta, V. R., Kubiak, C. P., Mahoney, W. J., Osifchin, R. G. (1996) Science 273, 1690-1693 "Self-assembly of a two-dimensional superlattice of molecularly linked metal clusters", Chen, E., Ahmed, H., Nakazoto, K. (1995) Appl. Phys. Lett. 66, 3383-3384 "Coulomb blockade at 77K in nanoscale metallic islands in a lateral nanostructure"). Ohmic charge transport has been observed in 3-dimensional arrays of Au and Ag nanoparticles. The resistance in such films can vary between $R>10^7\Omega$ to $R<10^2\Omega$, analogous to what has been observed in percolated films of metal grains depending on the grain size and the dot to dot distances (Musick, M. D., Keating, C. D., Keefe, N. H., Natan, M. J. (1997) Chem. Mater. 9, 1499-1501 "Stepwise construction of conductive Au colloid multilayers from solution", Neugebauer, C. A., Webb, M. B. (1962) J. Appl. Phys. 33, 74-82 "Electrical conduction mechanism in ultrathin, evaporated metal films").

WO 96/07487 describes the synthesis of nanoparticle materials exhibiting controlled electronic, magnetic and/or optical properties. Such synthesized materials can then be incorporated into electronic, magnetic and/or optical devices, such as, for example, resistors, diodes, transistors, switches, displays, lasers, photovoltaic and magnetic devices. Further, the application describes the production of thin film structures that can be used for said devices.

In addition, a 1-step formation of 3-dimensional nanoparticles is described via the preparation of a co-solution of nanoparticles and linker molecules and exposing this to a functionalized substrate. WO 96/07487 also describes a layer-by-layer assembly technique for producing thin film structures from particles of nanometer dimensions and polyfunctional linker molecules comprising a hydrocarbon skeleton with at least two functional groups (which may be the same or different) capable of binding to other particles or substrates.

WO 96/07487 further proposes a prototype of a nanostructured array of quantum dots with adjustable electronic conductivity in the range typical for semiconductors. The properties of the material can be tuned by building moieties into the linker molecules that can act as electron donors or acceptors. Further, the resistivity of the material changes dramatically as a function of the chain length of the linker molecule.

WO 96/07487 in general suggests activated electron hopping as the principle mechanism for charge transport.

Nevertheless, despite the above-mentioned progress, there is still the need in the art to improve multifunctional linker molecules in order to allow the tuning and/or fine tuning of the conductivity of nanostructured assemblies from the insulating to the conducting limit. Accordingly, the problem underlying the present invention is to provide improved multifunctional linker molecules for tuning the conductivity in nanoparticle-linker assemblies that may be used, e.g., in the formation of electronic networks and circuits and thin films of nanoparticles allowing a high-density arrangement.

The problem is solved according to the present invention by providing a multifunctional linker molecule of the general structure $$CON_1\text{-}FUNC_1\text{-}X\text{-}FUNC_2\text{-}CON_2$$

in which

X is the central body of the molecule, $FUNC_1$ and $FUNC_2$ independently of each other are molecular groups introducing a dipole moment and/or capable of forming intermolecular and/or intramolecular hydrogen bonding networks, and $CON_1$ and $CON_2$ (CON=connecting group or part) independently of each other are molecular groups binding to nanostructured units comprising metals or semiconductors.

The term "nanostructured" in the context of the invention refers to individual units, or an assembly of individual units, having at least one dimension less than 1 μm in size, preferably 100 nm or less in size. The nanostructured units may be generally described as spherical, rod-like, plate-like, tubular, belt-like, or wire-like, but they may also have other regular polyhedral or irregular geometric shapes. The nano-structured units may also be bi-layered or multi-layered, such as core-shell structures in the case of spherical particles.

It is to be understood that the term "nanoparticle" according to the scope of the invention is used generically. It includes all varieties of metal and semiconducting nanoparticles and "clusters". The sizes of the nanoparticles can vary between 0.8 nm and up to the order of a few 100 nm. Further, on the interconnecting, linker molecules can establish interconnects between at least two nanoparticles, between at least one nanoparticle and a nanowire, between at least two nanowires, nanotubes or nanobelts, as well as between at least one nanoparticle or one nanowire, nanotube or nanobelt and macroscopic electrodes. Thus, "assemblies" refers to one-, two-, and three-dimensional assemblies of the above mentioned systems in all possible combinations.

The term "nanocomposite" in the context of the invention refers to an assembly of nanostructured units interlinked by multifunctional linker molecules of the general structure $CON_1$-$FUNC_1$-X-$FUNC_2$-$CON_2$. Interlinking of the nanostructured units within the assembly occurs because the linker molecules can bind to one unit through group $CON_1$ and another unit through group $CON_2$. Binding of groups $CON_1$ and $CON_2$ to the nanostructured units occurs primarily through interaction of electron-donating atoms located on $CON_1$ and $CON_2$ with electron-accepting atoms located on the nanostructured units. This form of binding, in which molecular adsorption results from chemical bond formation, is known as "chemisorption". The electron-donating atoms on $CON_1$ and $CON_2$ in the invention comprise O, N, C, and S, and the particular electron-accepting atoms on the nanostructured units comprise the metal atoms (or metal ions) on the surfaces of metals and semiconductors. For applications of these nanocomposite materials in electronic devices, the electron-donating atoms on $CON_1$ and $CON_2$ may bind to metal atoms (or metal ions) on the surfaces of electrodes as well.

The invention is furthermore directed to utilizing multifunctional linker molecules with a particular novel group as $CON_1$ and $CON_2$ for binding to metal or semiconductor surfaces, i.e. the dithiocarbamate ester group. The general formula of these linker molecules is represented in the following structure, in which X is the central body of the molecule as described above. The substituents $R^1$ and $R^2$ on the N atoms may be H atoms or organic residues introducing a dipole moment and/or capable of forming intermolecular hydrogen bonding networks. The ester groups $R^3$ and $R^4$ may be alkyl or aryl residues. As noted in more detail below, the ester bond may cleave from the linker molecule when it binds to metal or semiconductor surfaces, so that the groups $R^3$ and $R^4$ are not present in the resulting assembly.

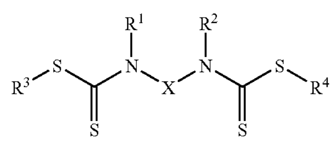

The dithiocarbamates and their related thiuram sulfide compounds can be considered as derivatives of the unstable compound dithiocarbamic acid, $H_2NCS_2H$. These compounds have been of great importance in the rubber industry where they have been used as vulcanization accelerators. Their importance in the biological field stems mainly from their properties as fungicides (Miller, C. R., Elson, W. O. (1949) J. Bacteriol. 57, 47-54 "Dithiocarbamic acid derivatives. I. The relation of chemical structure to in vitro antibacterial and antifungal activity against human pathogens"). More recently, dithiocarbamic acid derivatives have been employed as initiators for living free-radical polymerization reactions (Sebenik, A. (1998) Prog. Polym. Sci. 23, 875-917 "Living free-radical block copolymerization using thio-iniferters", Tsuji, S., Kawaguchi, H. (2004) Langmuir 20, 2449-2455 "Temperature-sensitive hairy particles prepared by living radical graft polymerization"). In general, the free dithiocarbamic acids are unstable, so that their use is restricted to their salt forms, which are stable in the dry state. Most dithiocarbamate salts have the general formulae $R^1NHCS_2M$ and $R^1R^2NCS_2M$, where $R^1$ and $R^2$ represent organic (alkyl or aryl) groups and M is a cation, typically $Na^+$ or $NH_4^+$. $R^1$ and $R^2$ may also be connected, i.e. to an organic ring system. Dithiocarbamic esters are another class of dithiocarbamic acid derivatives and have the general formulae $R^1NHCS_2R^3$ and $R^1R^2NCS_2R^3$, where $R^3$ represents an organic (alkyl or aryl) group. In contrast to the dithiocarbamic acids and salts, the esters are stable towards hydrolysis or thermal decomposition.

The inventors previously made the surprising discovery that linker molecules in which $CON_1$ and $CON_2$ are dithiocarbamate salts provide much more conductive nanocomposite films with gold nanoparticles than the analogous linker molecules in which $CON_1$ and $CON_2$ are thiols (Ford, W. E., Wessels, J. M., Yasuda, A. EP1215205A1 "Tuned multifunctional linker molecules for electronic charge transport through organic-inorganic composite structures and use thereof", Wessels, J. M., Nothofer, H.-G., Ford, W. E., von Wrochem, F., Scholz, F., Vossmeyer, T., Schroedter, A., Weller, H., Yasuda, A. (2004) J. Am. Chem. Soc. 126, 3349-3356, "Optical and electrical properties of three-dimensional interlinked gold nanoparticle assemblies"). This continuation-in-part is based on the even more surprising discovery that linker molecules in which $CON_1$ and $CON_2$ are dithiocarbamate esters provide nanocomposite films with gold nanoparticles whose electrical properties are comparable to those of the analogous dithiocarbamate salt based linker molecules.

Employing dithiocarbamate esters as $CON_1$ and/or $CON_2$ in multifunctional linker molecules offers several advantages over dithiocarbamate salts. Dithiocarbamate esters are characterized by a considerably greater stability towards hydrolysis or thermal decomposition compared to dithiocarbamate salts. The decomposition of the dithiocarbamate salts during the assembly process may alter the concentration of the linker molecules and may lead to introduction of impurities. Furthermore, assembly procedures performed at elevated temperatures may lead to decomposition of the dissolved dithiocarbamate salts even in neutral solution. It has long been known that dithiocarbamic acids are unstable compounds. Dithiocarbamate salts derived from primary amines undergo rapid decomposition in presence of an acid. In presence of a base they are converted to isothiocyanates. Dithiocarbamate salts derived from secondary amines are considered to be more stable, but possibly decompose when exposed to acidic conditions. (Thorn, G. D., Ludwig, R. A. (1962) "The Dithiocarbamates and Related Compounds" ISBN 0-444-40568-2, Cremlyn, R. J. (1996) in "An Introduction to Organosulfur Chemistry" ISBN 0-471-95512-4, Coucouvanis, D. (1970) Prog. Inorg. Chem. 11, 233-371 "The chemistry of the dithioacid and the 1,1-dithiolate complexes", Joris, S. J., Aspila, K. I., Chakrabarti, C. L. (1970) J. Phys. Chem. 74, 860-865, "On the mechanism of decomposition of dithiocarbamates").

The instability of both alkyl- and aryl-dithiocarbamate salts as well and the kinetics of the decomposition thereof has additionally been addressed by several recent publications (Humeres, E., Debacher, N. A., Marta de S. Sierra, J. M., Franco, D., Schutz, A. (1998) J. Org. Chem. 63, 1598-1603 "Mechanisms of acid decomposition of dithiocarbamates. 1. Alkyl dithiocarbamates", Humeres, E., Debacher, N. A., Marta de S. Sierra, J. M. (1999) J. Org. Chem. 64, 1807-1813, "Mechanisms of acid decomposition of dithiocarbamates. 2. Efficiency of the intramolecular general acid catalysis", Humeres, D., Debacher, N. A., Franco, J. D., Lee, B. S., Martendal, A. (2002) J. Org. Chem. 67, 3662-3667, "Mechanisms of acid decomposition of dithiocarbamates. 3. Aryldithiocarbamates and the torsional effect").

Due to the ionic structure of dithiocarbamate salts, the choice of solvents during the assembly of the nanocomposite is restricted to polar solvents, e.g. water, ketones, dimethylformamide, or dimethylsulfoxide. Nanostructured units, e.g. dodecylamine-stabilized gold nanoparticles are often dissolved in non-polar solvents, e.g. toluene. The non-miscibility between some of the polar solvents required for dissolution of dithiocarbamates and monolayer protected metal-nanoparticle solutions slows down the assembly process. Therefore a solution was sought to enable such assembly processes with dithiocarbamates or derivatives in a wide range of conditions, i.e. solvents of different polarity and at elevated temperatures.

The self-assembly process between dithiocarbamate esters and the nanostructured units can be performed in a wide range of solvents with different polarity and conditions, e.g. in either acidic or alkaline media. Furthermore the solubility of dithiocarbamate esters can be tuned by altering the ester groups.

The multifunctional linker molecule according to the invention has several advantages over the linker molecules described in WO 96/07487. First, the general structures are different in that the general structure of the linker of WO 96/07487 can schematically be seen as [Connecting group][Hydrocarbon skeleton][Connecting group], in which the connecting group is capable of binding to the nanostructured unit.

In contrast, the general structure of the multifunctional linker molecule according to the invention can be represented as [Connecting group 1][Functional group 1][Central body][Functional group 2][Connecting group 2] in which functional groups are introduced between the central body and the connecting groups which are capable of binding to nanoparticles. The functional groups introduce different specific functions into the inventive linker molecule and are not of hydrocarbon nature. Therefore, the molecular structure of the multifunctional linker molecule is different from WO 96/07487, which results in a drastic improvement of the capability for tuning the charge transport through organic/inorganic composite structures according to the invention.

The functional groups add the aspects of introducing a dipole moment into the structure and forming intermolecular and/or intramolecular hydrogen bonding networks. These features can support the ordering of the organic/inorganic composite structures and allows the tuning of the charge transport.

Thus, the design of the linker molecules according to the invention provides a means of tuning the conductivity through these assemblies. To the inventors' knowledge, so far a concept of how to alter molecular properties in order to tune the charge transport has not been suggested. This invention concerns a strategy for tuning the conductivity through such assemblies by altering specific parts of multifunctional linker molecules providing a molecular toolbox that allows tuning of the conductivity in such assemblies from the insulating to the conducting limit. This is again in contrast to WO 96/07487, which allows tuning of the conductivity only in the semiconducting range.

Preferred is a multifunctional linker molecule according to the invention, in which $CON_1$ and $CON_2$ are identical or different and $FUNC_1$ and $FUNC_2$ are identical or different.

In one embodiment, the multifunctional linker molecule according to the invention is characterized in that it exhibits a length between about 8 Å and about 30 Å.

Preferred is a multifunctional linker molecule according to the invention in which X is a structure having a hydrocarbon skeleton with two identical or different substituents that are used for connecting to and/or forming of the molecular groups $FUNC_1$ and $FUNC_2$.

The central part of the linker molecule can also consist of alkanes, alkenes, alkynes, and combinations thereof which exhibit two end groups comprising amines, carboxylic acids, sulfonic acids and phosphonic acids.

Further preferred is a multifunctional linker molecule according to the invention, which is characterized in that the substituents of X are selected from the group comprising amines, carboxylic acids, sulfonic acids and phosphonic acids. Even more preferred is, that the substituents of X are directed at an angle $\alpha$ relative to one another such that $90° < \alpha < 270°$.

In yet another embodiment of a multifunctional linker molecule according to the invention, X comprises a conjugated system, an aromatic $\pi$-system and/or contains heteroatoms, like N, O, or S, and/or contains at least one electron donating substituent, like $CH_3$, $O^-$, $COO^-$, $OCH_3$, $N(CH_3)_2$, or $NH_2$ and/or electron accepting substituent, like CN, $COCH_3$, $CONH_2$, $CO_2CH_3$, $N(CH_3)_3^+$, $NO_2$, F, Cl, Br, I, $OCF_3$, or $SO_2NH_2$.

Most preferred is a multifunctional linker molecule according to the invention, which is characterized in that X is selected from the group comprising a) linear or branched structures of alkanes, alkenes, alkynes and combinations thereof comprising 3-12 carbon atoms and exhibiting two end substituents as mentioned above;

b) structures having the general formula

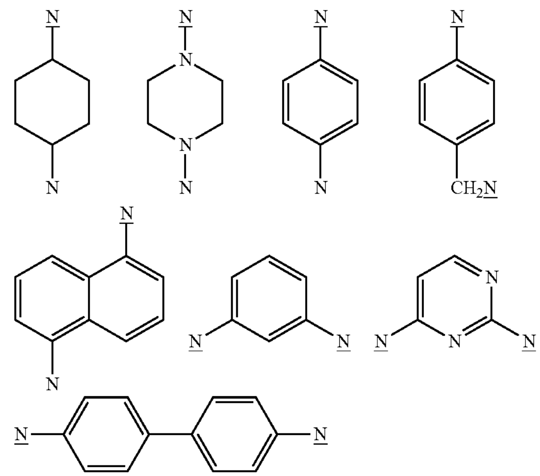

-continued

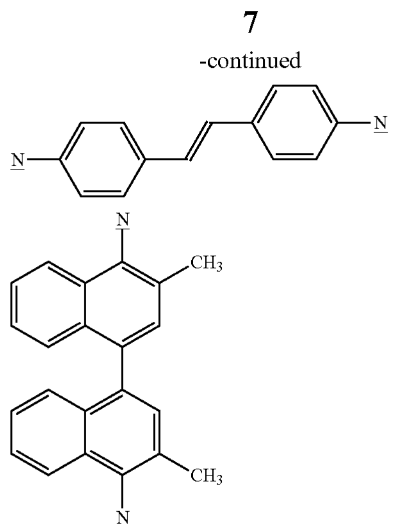

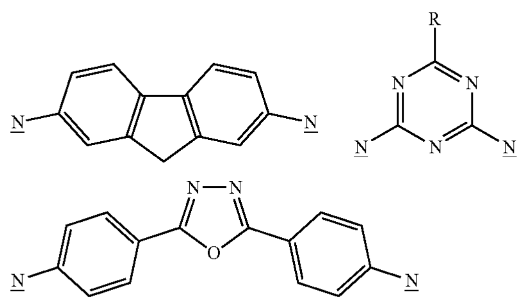

and derivatives thereof containing heteroatoms, like N, S, and/or O, or electron donating or accepting substituents; R can be methyl, phenyl or alkoxyl and wherein $FUNC_1$ and $FUNC_2$ are attached via the N-atoms of the two amine substituents indicated by N; structures having the general formula

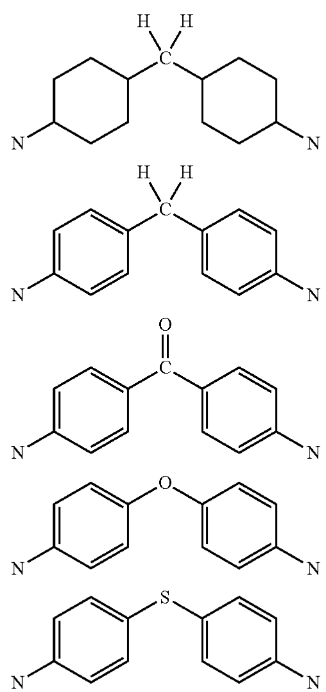

-continued

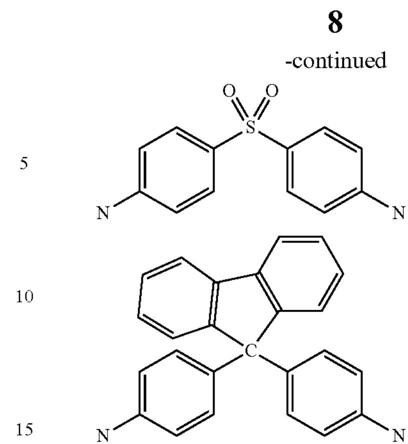

and derivatives thereof containing electron donating or accepting substituents wherein $FUNC_1$ and $FUNC_2$ are attached via the N-atoms of the amine substituents indicated by N; structures having the general formula

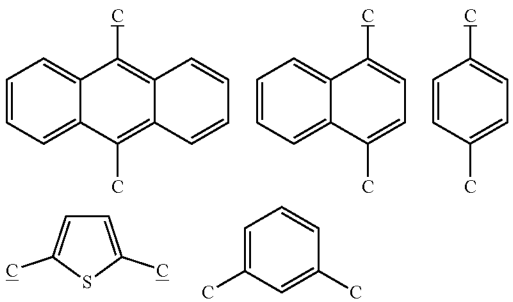

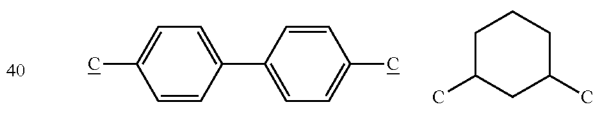

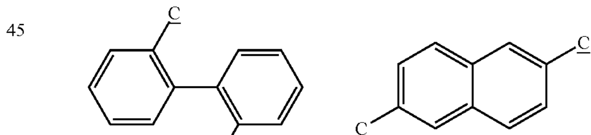

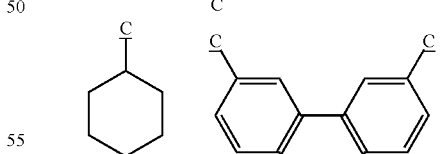

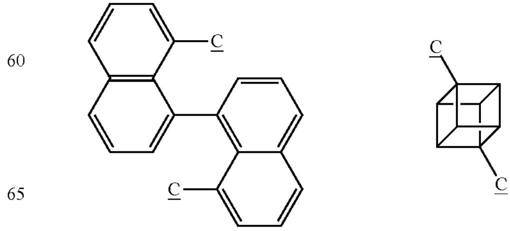

-continued

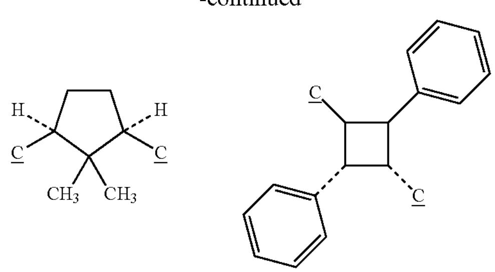

and derivatives thereof containing heteroatoms, like N, S, and/or O, or electron donating or accepting substituents; and wherein $FUNC_1$ and $FUNC_2$ are attached via the carbon atoms of the two carboxylic acid substituents indicated by C; structures having the general formula

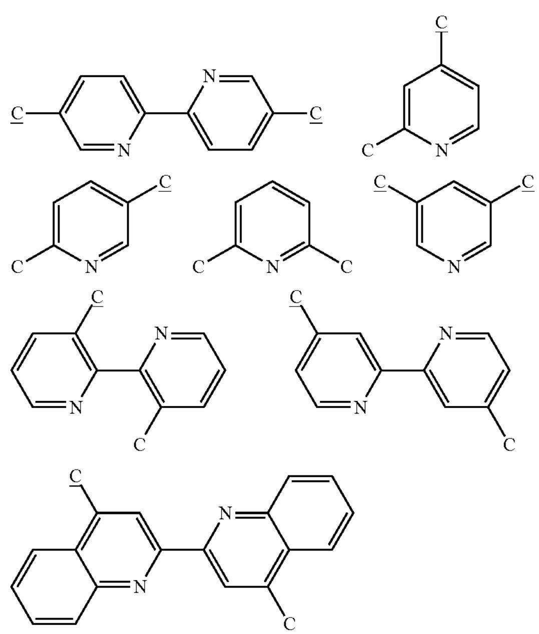

wherein $FUNC_1$ and $FUNC_2$ are attached via the carbon atoms of the two carboxylic acid substituents indicated by C; structures having the general formula

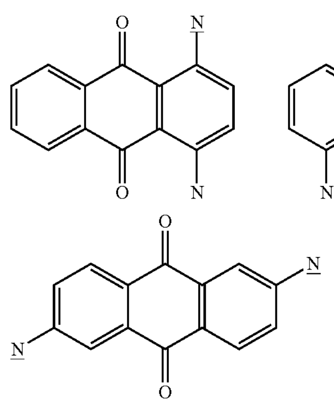

-continued

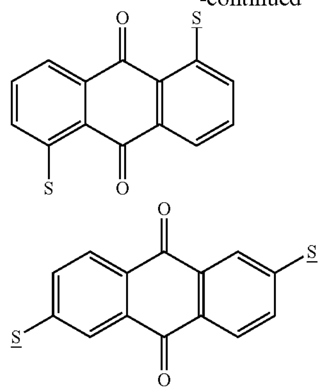

and derivatives thereof containing electron donating or accepting substituents wherein $FUNC_1$ and $FUNC_2$ are attached via the N- or S-atoms of the two amine or sulfonic acid substituents indicated by N and S; structures having the general formula

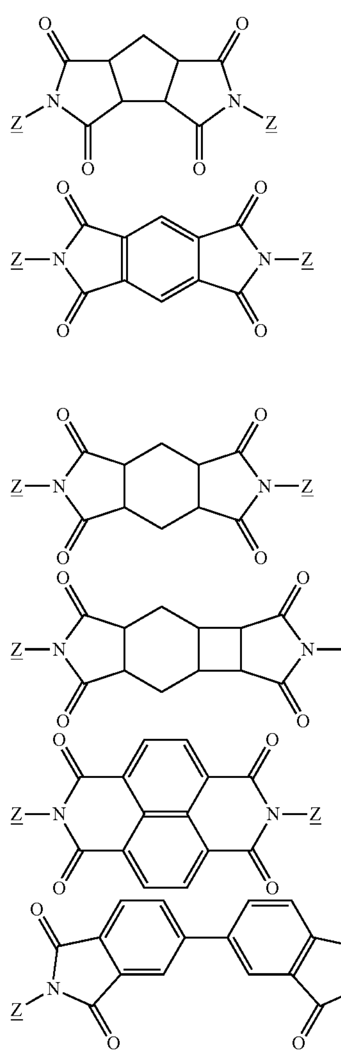

-continued

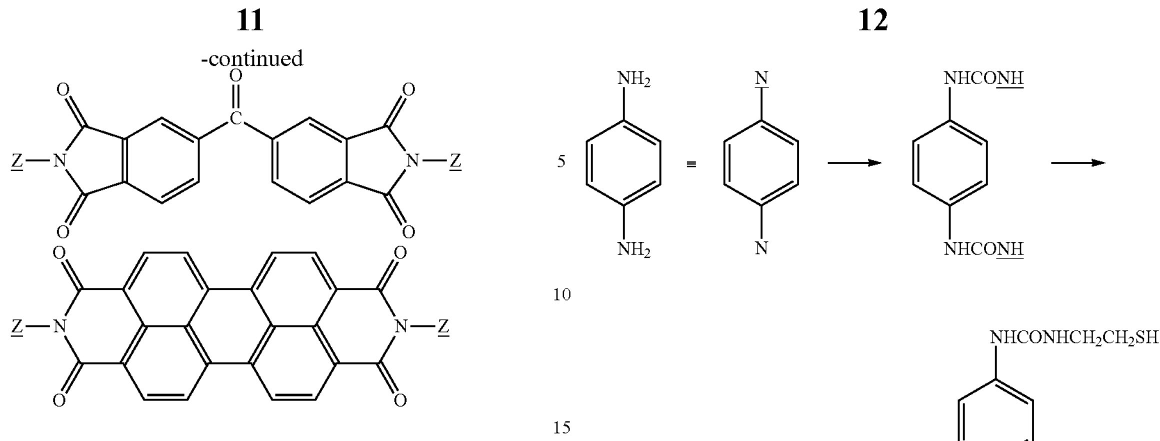

in which Z represents amine (Z=N) or a carboxymethyl (Z=CH(R)C) residue, wherein R is an amino acid side chain $FUNC_1$ and $FUNC_2$ are attached via Z; and c) electron donors like hydroquinones and electron acceptors, like quinones and diimides carrying two substituents as mentioned above.

In a still further embodiment according to the invention, the multifunctional linker molecule is characterized in that $FUNC_1$ and $FUNC_2$ independently of each other are connected to X via N, C, S, or P, and are selected from the group including —NH; —NHCO; —NHCONH, —NHCSNH, —NHCONHNH, —NHCSNHNH, —NHCONHNHCO, and —NHCONHNHCO in case of a connection via N;

—CONH, —CONHNH, and —CONHNHCO in case of a connection via C;

—$SO_2NH$, —$SO_2NHNH$, and —$SO_2NHNHCO$ in case of a connection via S; and

—$PO_2NH$, —$PO_2NHNH$, and —$PO_2NHNHCO$ in case of a connection via P.

In an even more preferred embodiment of a multifunctional linker molecule according to the invention, $CON_1$ and $CON_2$, connected to $FUNC_1$ and $FUNC_2$ via NH or CO, independently of each other are selected from the groups including —$(CHR)_n$COOH; —$(CHR)_n$NC; —$(CHR)_nNH_2$; —$(CHR)_nNHCS_2H$; —$(CHR)_nNHCS_2R'$;

—$(CHR)_nOPO_3H_2$; —$(CHR)_nOSO_3H$; —$(CHR)_nPO_3H_2$; —$(CHR)_n$SH; —$(CHR)_nSO_3H$; —CSOH;

—$CS_2H$, and $CS_2R'$ in case of a connection via NH; and

—$(CHR)_n$COOH; —$(CHR)_n$NC; —$(CHR)_nNH_2$; —$(CHR)_nNHCS_2H$; —$(CHR)_nNHCS_2R'$;

—$(CHR)_nOPO_3H_2$; —$(CHR)_nOSO_3H$; —$(CHR)_nPO_3H_2$; —$(CHR)_n$SH; and —$(CHR)_nSO_3H$ in case of a connection via CO;

where R is H, $CH_2OH$, or $CH_3$, n is 1 or 2, and R' is an alkyl or aryl group.

It is to be understood that, for simplicity, the above formulations of $CON_1$ and $CON_2$ represent the free acid forms, but salt (ionic) forms are equally intended or preferred. The acidic protons of these various groups are generally released upon binding to metal or semiconductor, so the structure of the nanocomposite is largely independent of whether one uses the linker molecule in its free acid or salt form.

One example of how the different units can be put together can schematically be described as follows:

In a further embodiment of the inventive multifunctional linker molecule, the dithiocarbamate salts or dithiocarbamate esters formed from secondary amines are directly attached to the central body X.

Other preferred embodiments of the inventive multifunctional linker molecule are characterized in that $CON_1$ and $CON_2$ independently of each other comprise branched molecular structures.

Other preferred embodiments of the multifunctional linker molecule according to the invention are selected from the group of the following formulae:

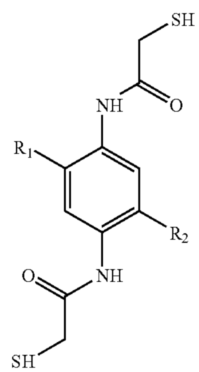

in which $R_{1,2}$ is independently selected from H (1), $CH_3$ (2) and/or Cl (3), 1,4-dimercaptoacetamidocyclohexane, having the formula (4)

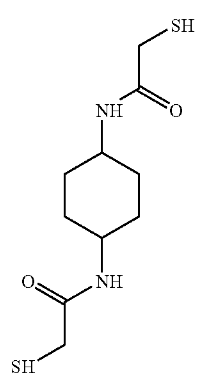

1,4-dimercaptoacetamido-9,10-anthraquinone, having the formula (5)

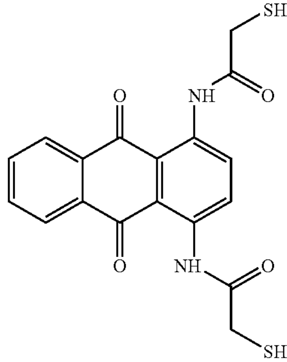

1,5-dimercaptoacetamido-9,10-anthraquinone, having the formula (6)

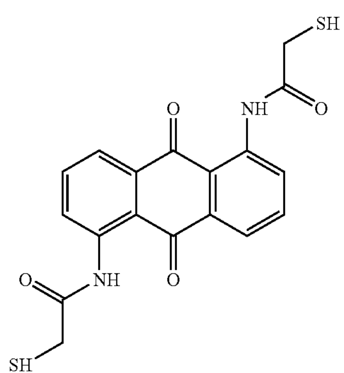

1,8-dimercaptoacetamidooctane, having the formula (9)

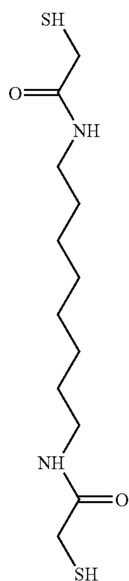

1,4-bisdithiocarbamates and derivatives, having the formulae (7)

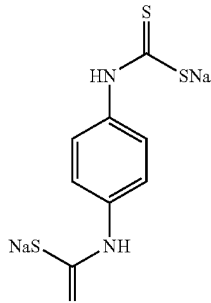

(8)

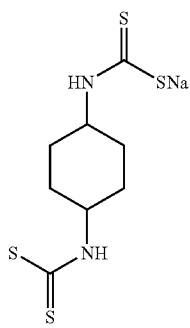

and 1,4-bisdithiocarbamate esters and derivatives, having the formulae (11)

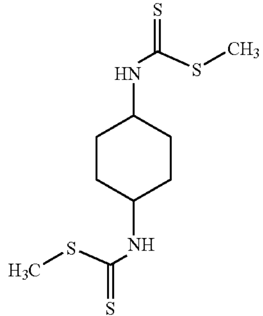

(12)

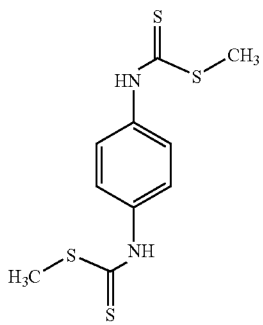

In an even more preferred embodiment of the invention, the multifunctional linker molecule is characterized in that the electron density on aromatic π-systems, as it can be described through the Hammett correlation parameter, and/or the degree of conjugation of the linker molecule is altered.

Another aspect of the invention is a 1-, 2-, or 3-dimensional assembly of nanostructured units comprising a multifunctional linker according to the invention wherein the conductivity of the assembly is determined by the structure of the multifunctional linker molecule.

Preferably, the assembly according to the invention is characterized in that the nanostructured units are selected from the group comprising nanostructured units, such as metal, semiconductor, or core/shell semiconductor nanoparticles, nanowires, nanotubes, nanobelts, and electrodes.

The problem of the invention is further solved by an assembly, which is characterized in that the absorption of the plasmon band is located between 500 nm and 600 nm, the functional units are Au-nanoparticles, the size of said Au-nanoparticles is about 5 nm to about 20 nm, the resistivity of the assembly is of the order of $10^2$ Ωcm for a film thickness of about 30 nm, and the resistivity increases with decreasing temperature.

More preferred is an assembly which is characterized in that the absorption maximum of the plasmon band is located between 600 nm and 700 nm, the functional units are Au-nanoparticles, the size of said Au-nanoparticles is about 5 nm to about 20 nm, the resistivity of the assembly is of the order of $10^{-1}$ Ωcm to 10 Ωcm for a film thickness of about 30 nm, and the resistivity increases with decreasing temperature.

Most preferred is an assembly according to the invention which is characterized in that the absorption spectrum shows the absorption characteristics of bulk metal films, the functional units are Au-nanoparticles, the size of said Au-nanoparticles is about 5 nm to about 20 nm, the resistivity of the assembly is of the order of $10^{-2}$ Ωcm for a film thickness of about 30 nm, and the resistivity decreases with decreasing temperature.

In a still further aspect of the invention, the problem is solved by the use of an assembly according to the invention as interconnects between nanowires and nanostructured units in 1-, 2- and 3-terminal devices, self-assembled metal coatings and/or self-assembled electrodes.

The inventors of the present application have surprisingly found that a new design of nanoparticle linker molecules allows the effective tuning of the charge transport in nanoparticle linker assemblies from the insulating to the conducting limit.

The present invention provides a method for tuning the charge transport through such assemblies by altering specific parts of the multifunctional linker molecules, which provides a molecular toolbox that allows tuning of the charge transport in such assemblies from the insulating to the conducting limit. To the inventors' knowledge, so far a concept of how to alter molecular properties in order to tune the charge transport has not been suggested.

Tuning of the charge transport is in one embodiment achieved by altering the energy levels of the molecular orbitals and the bonds formed between the nanoparticle and linker molecule.

Four different means for altering the multifunctional linker molecules for tuning the charge transport through these assemblies are considered in this invention:

1) Altering of the electron density on aromatic π-systems through different substituents as it can be described through the Hammett correlation parameter $\sigma_p^+$.

It is important for the design of nanostructured electronic devices to have means for fine tuning the HOMO-LUMO levels of the linker molecules, in order to adjust the HOMO and LUMO levels of the linker molecules with respect to the Fermi energy level of metal particles as well as the energy band levels of semiconducting particles. In this invention, we provide a new approach for providing a series of linker molecules exhibiting an aromatic π-system where the electron density on the aromatic π-system of the multifunctional linker molecule is varied in a defined manner as it can be described by the so-called Hammett correlation parameter $\sigma_p^+$. This parameter describes the electron donating and accepting properties of substituents on aromatic π-systems, which alters the energy gap between the HOMO and LUMO energy levels in the linker molecules, and hence provides a means for fine-tuning the charge conduction through the assemblies.

2) Altering the degree of charge transport through linker molecules exhibiting conjugated π-systems.

a) Altering the particle-particle interaction by changing the degree of conjugation in the linker molecule through cross-conjugation and/or by introducing non-conjugated molecular structures into the linker molecule.

b) Introducing electron-accepting groups onto conjugated π-systems of the linker molecule, facilitating the electron transport across the linker molecule.

The possibilities for influencing charge transport by changing the degree of delocalization in conjugated π-systems via cross-conjugation has been suggested for molecular wires. Theoretical calculations have shown that in case of molecular wires made out of coupled porphyrin systems, cross conjugation leads to a pronounced attenuation of the coupling interaction between HOMO-orbitals (Hush, N. S., Reimers, J. R., Hall, L. E., Johnston, L. A., Crossley, M. J. (1998) Ann. New York Acad. Sci. 852, 1-21 "Optimization and chemical control of porphyrin-based molecular wires and switches"). Cross-conjugation interrupts the long-range electronic coupling of conjugated π-bonds and hence it is a possibility to fine-tune the conductivity of linker molecules exhibiting conjugated π-systems.

Besides the possibility of influencing the charge transport in conjugated linker molecules via cross-conjugation the charge transport can also be altered by introducing electron-accepting groups into the linker molecules. Quinones are very efficient electron acceptors that are implemented into the light harvesting systems of plants. It has been suggested that they have been developed by the plants in order to facilitate electron transport in the photosynthetic system. Similarly it can be envisioned that efficient electron acceptors such as anthraquinones (Karuktis, K. K., Gruber, S. M., Fruetel, J. A., Boegeman, S. C. (1988) Biochim. Biophys. Acta 932, 84-90 "Quenching of chlorophyll fluorescence by substituted anthraquinones") for example can facilitate the electron transport in such multidimensional assemblies.

3) Influencing the charge transport properties through the contacting molecular groups $CON_{1,2}$.

The molecular groups forming the connection between the different nanostructured units, e.g. wires, active elements, and possibly electrodes have a central function in the charge transport, since the molecular design of this group is defining the type of bond that is formed the linker molecule and the different nanostructured units. Included is also, that the electrode or wire metal can be altered to alter the atom from the nanostructured unit that participates in forming the contact to the linker molecule depending on what type of tunnel barrier should be established for a specific interconnect.

The role of the contacts has been studied theoretically by implementing the contact to Au-particles into the extended calculations of the HOMO and LUMO levels of a 1,4-benzene dithiolate (Emberly, E. G., Kirczenow, G. (1998) Ann. New York Acad. Sci. 852, 1-21 "Theory of electrical conductance through a molecule"). These calculations show that, in a model system consisting of two Au-particles connected by one benzene dithiolate, conduction can occur via two pathways:

a) Through the states derived from the benzene dithiolate HOMO and LUMO levels.

b) Through the energy levels arising from hybrid Au particle-benzene dithiolate states.

However, the linker molecule/particle interface has a very low density of states. Experiments by Reed et al. suggest that the contacts are atomically terminated, i.e. the S-atoms are attached to single Au-atoms (Reed, M. A., Zhou, C., Mueller, C. J., Burgin, T. P., Tour, J. M. (1997) Science 278, 252-254 "Conductance of a molecular junction"). It has been shown for Au—S systems that the Au atoms co-contribute s states while the S atoms contribute p states, thereby forming σ bonds (Di Ventra, M., Pantelidis, S. T., Lang, N. D. (2000) Phys. Rev. Lett. 84, 979-982 "First-principles calculation of transport properties of a molecular device", Johansson, A., Stafström, S. (2000) Chem. Phys. Lett. 322, 301-306 "Interactions between molecular wires and a gold surface"). Thus, the linker molecule/particle interface forms a tunnel barrier for the charge transport. Therefore, binding of the linker molecule via single or multiple binding groups, e.g. thiols or dithiocarbamates, should have a strong influence on the properties of the tunnel barrier and hence on the charge transport through these assemblies.

It has been shown that dithiocarbamates provide an excellent coupling between metals and molecules (Wessels, J. M., Nothofer, H.-G., Ford, W. E., von Wrochem, F., Scholz, F., Vossmeyer, T., Schroedter, A., Weller, H., Yasuda, A. (2004) J. Am. Chem. Soc. 126, 3349-3356, "Optical and electrical properties of thee-dimensional interlinked gold nanoparticle assemblies"). It is also known that dithiocarbamates bind strongly to the surface of semiconductors such as CdS and CdSe (Thackery, J. W., Natan, M. J., Ng, P., Wrighton, M. S. (1986) J. Am. Chem. Soc. 108, 3570-3577 "Interaction of diethyldithiocarbamate with n-type cadmium sulfide and cadmium selenide: Efficient photoelectrochemical oxidation to the disulfide and flat-band potential of the semiconductor as a function of adsorbate concentration").

This invention also concerns a strategy for employing dithiocarbamate esters as novel multifunctional linking molecules containing the dithiocarbamate moiety for the preparation of nanoelectronic devices. Dithiocarbamate esters are well known to be exceptionally stable under acidic or alkaline conditions and are even considered to be more stable than their O-analogues (Thorn, G. D., Ludwig, R. A. (1962) "The Dithiocarbamates and Related Compounds" ISBN 0-444-40568-2, Cremlyn, R. J. (1996) in "An Introduction to Organosulfur Chemistry" ISBN 0-4719-5512-4). Furthermore, dithiocarbamate esters can be used in solutions at elevated temperatures without decomposition, and their solubility in different solvents can be tuned by altering the nature of the ester group. Despite the intrinsic stability of the ester bond, the inventors have surprisingly found that the dithiocarbamate esters, like the dithiocarbamate salts, provide low-ohmic contacts in composite assemblies with gold nanoparticles.

Further, theoretical calculations have shown that replacement of Au atoms by Al atoms should reduce the tunnel barrier. Al atoms can contribute to the interconnect p-orbitals and thus are capable to form π-orbitals with S atoms of linker molecules (Di Ventra, M., Pantelidis, S. T., Lang, N. D. (2000) Phys. Rev. Lett. 84, 979-982 "First-principles calculation of transport properties of a molecular device").

4) Influencing the charge transport by altering the functional groups of the linker molecule that is located at the nanoparticle/linker molecule interface, i.e. increasing the electron coupling through two interconnected circuit elements by introducing a hydrogen-bonding network into the linker molecules.

It has been shown that a hydrogen bond network linking amide bonds in alkane monolayers leads to an increase in the electronic coupling between an electrode and a ferrocene molecule (Se, S., Misicha, A., Bileicz, R. (2000) J. Phys. Chem. B 104, 5399-5402 "Effect of interchain hydrogen bonding on electron transfer through alkanethiol monolayers containing amide bonds"). The same effect has also been observed for the electron tunneling across alkane-thiolate bilayers at mercury-mercury junctions (Slowinski, K., Fong, H. K., Mayda, M. (1999) J. Am. Chem. Soc. 121, 7257-7261 "Mercury-mercury tunneling junctions. 1. Electron transfer across symmetric and asymmetric alkane thiolate bilayers").

When thiol compounds (e.g., RSH) bind to gold surfaces in, e.g., self-assembled monolayers, it is thought that $H_2$ is evolved as a result of deprotonation of thiol molecules and simultaneous oxidation of Au atoms. The net reaction is indicated in the following equation, where $(Au)_n$ represents elemental gold.

$$RSH+Au(Au)_n \rightarrow RS^- + Au^+(Au)_n + \tfrac{1}{2}H_2.$$

The bonding between the thiolate anion, $RS^-$, and $Au^+ (Au)_n$ can be viewed in two extremes. In one extreme, the bonding is purely electrostatic ($RS^-Au^+ (Au)_n$). In the other extreme, the bonding is purely covalent ($RS—Au(Au)_n$). The actual mode of bonding should probably be viewed as intermediate between these two extremes.

A similar situation exists when dithiocarbamic acid salts (e.g., $R^1NHCS_2Na$) bind to gold surfaces, except that two S atoms may be involved in the binding process instead of one. Since the two S atoms are equivalent due to resonance in the dithiocarbamate anion, binding to gold is likely to occur through both S atoms. This expectation is supported experimentally by XPS and theoretically. Purely electrostatic and purely covalent bonding between dithiocarbamate anion and gold are illustrated schematically in FIG. 1_a_ and FIG. 1_b_, respectively.

As of yet, there have been no investigations of the mechanism or the nature of the Au—S bond in nanocomposite assemblies comprising gold nanoparticles and dithiocarbamate esters. Therefore, it is uncertain whether the ester bond remains intact or is cleaved during the assembly process. While not wishing to be bound to theory, several possibilities can be proposed. If the ester bond remains intact, bonding could occur through both S atoms by sharing their lone pair electrons with Au atoms on the surface. Purely electrostatic binding analogous to that described above for dithiocarbamate salts would be possible as a result of deprotonation of the N atom, as indicated in FIG. 1_c_, whereas the purely covalent binding mode is indicated in FIG. 1*d*. However, the remarkable similarities between nanocomposite assemblies obtained from dithiocarbamate esters and gold nanoparticles to those obtained from the corresponding dithiocarbamate salts indicate that the product is the same in both cases, thereby indicating that the ester bond is cleaved during the assembly process.

It is known that the thioacetyl bond cleaves when acetyl-protected thiols (e.g., $RSC(O)CH_3$) bind to gold surfaces, giving the same surface-bound thiolate species as is obtained directly from the parent thiol compounds. This reaction can occur spontaneously or be promoted by a base, e.g. $NH_4OH$ (Tour, J. M., Jones, L., Pearson, D. L., Lamba, J. J. S., Burgin, T. P., Whitesides, G. M., Allara, D. L., Parikh, A. N., Atre, S. (1995) J. Am. Chem. Soc. 117, 9529-9534 "Self-assembled monolayers and multilayers of conjugated thiols, αω-dithiols, and thioacetyl-containing adsorbates. Understanding attachments between potential molecular wires and gold surfaces"). Without being bound to theory, it is anticipated that a comparable reaction may take place when combining dithiocarbamate esters with nanoparticles or attaching them to a gold surface. The hydrolysis of the dithiocarbamate esters, via trace amounts of water, is a plausible reaction course for the subsequent bond formation between the dithiocarbamate ester and the metal. The net reaction is indicated in the following equation.

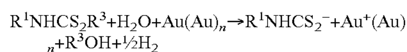

$$R^1NHCS_2R^3+H_2O+Au(Au)_n \rightarrow R^1NHCS_2^-+Au^+(Au)_n+R^3OH+\tfrac{1}{2}H_2$$

The investigation of bond formation remains to be done and might be important when considering the choice of $R^3$.

An important advantage of using dithiocarbamate esters instead of dithiocarbamate salts as linker molecules for the assembly of one-, two-, or three-dimensional organic-inorganic nanocomposites is that the esters exhibit a considerably increased stability towards acidic or alkaline conditions, thereby avoiding the formation of impurities during the assembly process. Furthermore, the solubility of dithiocarbamate esters in solvents of a wide range of polarities can be tuned by appropriately choosing the ester group $R^3$, whereas the solubility of dithiocarbamate salts is limited mainly to polar solvents. To the knowledge of the inventors, the use of polyfunctional dithiocarbamate esters for the self-assembly of nanocomposite materials has not been described up to now.

Various types of metal or semiconducting nanoparticles can be interconnected into one-, two-, or three-dimensional arrays of nanoparticles. The synthesis of various nanoparticles is described in the literature as well as in patents. Depending on the preparation method and the capping molecule used, the nanoparticles can be prepared exhibiting different sizes. The preparation methods as well as the capping molecule largely determine the size distribution of the nanoparticles. A requirement for the successful assembly of the nanoparticles into an array is that the linker molecule can readily displace the capping molecule. In case a particular capping molecule can not be displaced by the linker molecules, the capping molecule could be exchanged with a different kind of capping molecule in a ligand exchange reaction prior to the assembly process (Jahn, W. (1999) J. Struct. Biol. 127, 106-112 "Review: Chemical aspects of the use of gold clusters in structural biology", Brown, L. O., Hutchinson, J. E. (1997) J. Am. Chem. Soc. 119, 12834-12835 "Convenient preparation of stable, narrow-dispersity, gold nanocrystals by ligand exchange reactions", Aguila, A., Murray, R. W. (2000). Langmuir 16, 5949-5954 "Monolayer-protected clusters with fluorescent dansyl ligands").

The synthesis of the multifunctional, i.e. bi-, and polyfunctional linker molecules, is based on substitution reactions that are described in the literature. Two possible synthetic routes are considered. In route 1, the amino substituents of the starting materials are converted into bromoacetamido groups via a nucleophilic substitution reaction with bromoacetylbromide. In the second step, the bromoacetamido group is converted into a thioacetate ester by reaction with potassium thioacetate. The thioacetate ester is converted into a thiol via a cleavage reaction as it is described by Yelm (Yelm, K. E. (1999) Tetrahedron Lett. 40, 1101-1102 "A simple method for in situ generation of thiols from thioacetates") as well as Wallace and Springer (Wallace, O. B., Springer, D. M. (1998) Tetrahedon Lett. 39, 2963-2964 "Mild, selective deprotection of thioacetates using sodium thiomethoxide"). Alternatively, the reaction can be carried out as described by Martin and Comer (Martin, T. A., Corner, W. T. (1985) J. Med. Chem. 28, 910-914 "N-[[(Mercaptoacetyl)amino]benzoyl]glycines as mucolytic agents") in an aqueous methanolic NaOH solution. The reaction is shown in FIG. 2*a* (prior art).

In route 2, the amino substituents are directly reacted with carbon disulfide and base to give dithiocarbamate salts. This reaction is described in references (McCubbin, Q. J., Stoddart, F. J., Welton, T., White, A. J. P. L., Williams, D. J. (1998) Inorg. Chem. 37, 3753-3758 "Dithiocarbamate-functionalized dendrimers as ligands for metal complexes", Almirall, E., Fragoso, A., Cao, R. (1999) Electrochem. Commun. 1, 10-13 "Molecular recognition of a self-assembled monolayer of a polydithiocarbamate derivative of β-cyclodextrin on silver", Matsumoto, I., Nakagawa, K., Matsuzaki, M., Horiuchi, K. (1975), U.S. Pat. No. 3,875,170 "Pyridine bis(dithiocarbamate)derivatives"), as is depicted in FIG. 2*b* (prior art).

This invention solves several of the difficulties associated with the preparation of one-dimensional, two-dimensional, and three-dimensional assemblies of metal or semiconducting nanoparticles interconnected by dithiocarbamates. The invention refers to the class of polyfunctional dithiocarbamate esters prepared in a conventional manner according to literature procedures. These compounds serve as vulcanization accelerators, antioxidants in the rubber industry and are widely employed as agricultural fungicides. To the inventor's best knowledge, dithiocarbamate esters have never been used before in the preparation of three-dimensional interlinked metal-nanoparticle networks or in the formation of organic-inorganic nanocomposites.

Dithiocarbamate salts are easily prepared by the reaction of amines with carbon disulfide:

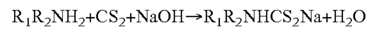

$$R_1R_2NH_2+CS_2+NaOH \rightarrow R_1R_2NHCS_2Na+H_2O$$

The synthesis of aryl-bis-dithiocarbamate salts requires a different procedure described in the literature and in patents (Kobayashi, N., Osawa, A., Kimoto, H., Hayashi Y., Shimizu, K., Fujisawa T. (1977) J. Polym. Sci. 15, 39-49 "Sulfur-containing polymers. XVIII. Preparation and properties of thiuram polysulfide polymers", van der Kerk, G. J. M., Pluygers, C. W., de Vries, G. (1955) Recueil 74, 1262-1268 "A new method for the preparation of aromatic isothiocyanates", Söder, A., Lämmler, G. DBP1134063 "Verfahren zur Herstellung von Acryl-bis-dithiocarbamaten", Reisener, H. DE 1020481A "Fungizides Mittel"). Such compounds contain the dithiocarbamate moiety in its anionic form (i.e. as salts) with a counterion comprising, e.g., $Na^+$ or $NH_4^+$. However, as already noted, dithiocarbamate salts are relatively chemically unstable, especially in the solution phase.

The functional group interconversion from dithiocarbamate salt to dithiocarbamate ester is a facile procedure and easily achieved according to procedures given in the literature (Thorn, G. D., Ludwig, R. A. (1962) "The Dithiocarbamates and Related Compounds" ISBN 0-444-40568-2, Klöpping, H. L., van der Kerk, G. J. M. (1951) Recueil 70, 917-939 "Investigations on organic fungicides IV", Klöpping, H. L., van der Kerk, G. J. M. (1951) Recueil 70, 949-961 "Investigations on organic fungicides V", Kobayashi, N., Osawa, A., Kimoto, H., Hayashi Y., Shimizu, K., Fujisawa T. (1977) J. Polym. Sci. 15, 39-49 "Sulfur-containing polymers. XVIII. Preparation and properties of thiuram polysulfide polymers", Mizuyama, K., Tominaga, Y., Matsuda, Y., Kobayashi, G. (1979) Chem. Pharm. Bull. 27, 2879-2889 "Synthesis and reactions of heterocyclic dithiocarbamates", Buess, C. M. (1955) J. Am. Chem. Soc. 77, 6613-6615 "The reaction of dithiocarbamates with acrylamides", Giboreau, P., Morin, C. (1994) J. Org. Chem. 59, 1205-1207 "Procedure for the preparation of pure dithiocarbamates"). A convenient way to prepare dithiocarbamate esters is a one-pot procedure starting from the dithiocarbamate: $R_1R_2NHCS_2Na+R^3L \rightarrow R_1R_2NHCS_2R^3+NaL$, where L represents a good leaving group such as Br or I.

Using these procedures allows the synthesis of a variety of target linker molecules having the following general formula, in which X is the central body of the molecule.

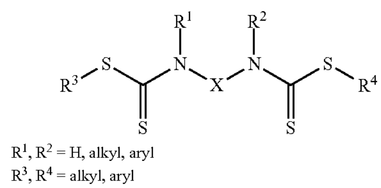

Choosing appropriate ester groups, $R^3$, $R^4$ allows for adapting the polarity and/or solubility of the dithiocarbamate esters. The ester groups $R^3$ and $R^4$ may vary from non-polar alkyl chains to highly polar groups, e.g. ones containing COOH residues. Therefore, the self-assembly process between the dithiocarbamate esters and the monolayer-protected metal-nanoparticles can be adapted to the specific solubility of the metal-nanoparticles to ensure a highly efficient, i.e. fast, assembly process. The dithiocarbamate ester group serves as $CON_{1,2}$ may be attached either directly or via an additional functional unit $FUNC_{1,2}$. The ester moiety is preferably an alkyl chain consisting of $C_1$-$C_{20}$ carbon atoms or an alkyl chain to which a conjugated group is attached (e.g., benzyl group) or an alkyl chain to which another functional group is attached to alter, e.g., the polarity of the molecule.

Various means for assembling nanocomposite thin films comprising nanoparticles and linker molecules have been described in the literature and in patents. The first layer of nanoparticles can be deposited onto a substrate by means of self-assembling bi-functional organic monolayers as bridge compounds. The first layer of nanoparticles can self-assemble on the functional substrate and be subsequently interconnected by the linker molecules. The linker molecules displace the capping molecules from the surface of the nanoparticles leaving a free linker group, e.g. a thiol group at the top of the nanoparticle film for the assembly of the next nanoparticle layer. This assembly process is also referred to as the layer-by-layer assembly technique (Brust, M., Bethell, D., Kiely, C. J., Schiffrin, D. J. (1998) Langmuir 14, 5425-5429 "Self-assembled gold nanoparticle thin films with non-metallic optical and electronic properties"). Alternatively, a one-step formation of 3-dimensional nanoparticles can be achieved via the preparation of a co-solution of nanoparticles and linker molecules and exposing this to a functionalized substrate (Whetten, R. L., Khoury, J. T., Alvarez, M. M., Murthy, S., Vezmar, I., Wang, Z. L., Stephens, P. W., Cleveland, C. C., Luedtke, W. D., Landman, U. (1996) Adv. Mater. 8, 428-433 "Nanocrystal gold molecules"). A close-packed monolayer of nanoparticles can also be produced using the Langmuir-Blodgett or the Langmuir-Schaeffer technique (Musick, M. D., Keating, C. D., Keefe, N. H., Natan, M. J. (1997) Chem. Mater. 9, 1499-1501 "Stepwise construction of conductive Au colloid multilayers from solution", Markovich; G., Leff, D. V., Chung, S.-W., Soyez, H. M., Dunn, B., Heath, J. R. (1997) Appl. Phys. Lett. 70, 3107-3109 "Parallel fabrication and single-electron charging of devices based on ordered, two-dimensional phases of organically functionalized metal nanocrystals"). These techniques allow the transfer of a well-defined monolayer to a substrate, the packing density of which can be determined through the compression of the nanoparticle film at the air-water interface. Instead of using multifunctional organic molecules as bridge compounds it is also possible to deposit e.g. charged nanoparticles onto a substrate utilizing electrostatic interactions (Ahmed, H., Sato, T. (1998) EP 0 865 078 "Method of depositing nanometer scale particles").

For certain metal particles, the assembly process can be monitored using absorption spectroscopy. The optical density of the plasmon band provides information about the thickness of the self-assembled film. Furthermore, depending on the material and composition of the nanoparticles, the absorption spectrum contains also information about the character of the nanoparticle film, since the optical properties of the particles are determined by the contributions from the individual particles and the collective properties of the ensemble. The plasmon band is attributed to the collective oscillations of the free conduction electrons and their response to an incident electromagnetic field. It can be considered as a hybrid resonance from the co-operative behaviour of the d-band and conduction electrons. A simple description of the plasmon frequency combining the resonance condition and the dielectric constant for a free electron gas is:

$$\varpi_{max} = \frac{ne^2}{\varepsilon_0 m_{eff}\sqrt{1+\varepsilon_m}}$$

where n denotes the electron density and $m_{eff}$ the effective mass of the electron. It has been shown in the literature, that the material dielectric function which includes core polarization effects and the full Mie expression have to be used to describe the surface plasmon absorption correctly (Link, S., Wang, Z. L., El-Sayed, M. A. (1999) J. Phys. Chem. 103, 3529-3533 "Alloy formation of gold-silver nanoparticles and the dependence of the plasmon absorption on their composition", Alvarez, M. M., Khoury, J. T., Schaaff, T. G., Shafigulli, M. N., Vezmar, I., Whetten, R. L. (1997) J. Phys. Chem. 101, 3706-3712 "Optical absorption spectra of nanocrystal gold molecules"). Included into the description of the plasmon frequency is the dependence on the electron density and on the effective mass or optical mass of the electron, which includes the coupling of the free electrons to the ion core (Kreibig, U., Genzel, L. (1985) Surf. Sci. 156, 678-700 “Optical absorption of small metallic particles”). Thus, it is possible to gain some information about the electronic interaction of particles in the assembly from the absorption spectrum. For semiconducting nanoparticles, the band-gap absorption can be used for monitoring the assembly process.

The electrical properties of such one-, two, or three-dimensional arrays of nanoparticles are determined by material composition and size of the nanoparticles used, the stabilizing organic ligand, and by the properties of the linker molecules. Arranging small particles into an array exhibiting small spatial distance, tunnel junctions exhibiting an electrical capacitance of less than $10^{-18}$ F are created (Devoret, M. H., Grabert, H., Eds. (1992) “Single Charge Tunneling—Coulomb Blockade Phenomena in Solids” NATO ASI Series, Vol. 294). The insulating molecular layer around the nanoparticle that serves as an insulating barrier facilitates electron tunneling or hopping. The charge transport in these structures can be tuned from the metallic to the insulating limit by varying the size of the particles and the strength of the coupling between them.

The electron transport properties of these thin films depend on the properties of the insulating layer and the linker molecules (Brust, M., Bethell, D., Kiely, C. J., Schiffrin, D. J. (1998) Langmuir 14, 5425-5429 “Self-assembled gold nanoparticle thin films with nonmetallic optical and electronic properties”, Neugebauer, C. A., Webb, M. B. (1962) J. Appl. Phys. 33, 74-82 “Electrical conduction mechanism in ultrathin, evaporated metal films”). Activation energies in the range between 30-100 meV, depending on the electronic structure of the linker molecule, the dot-to-dot distance, and the size of the nanoparticles, have been reported for such assemblies (Brust, M., Bethell, D., Schiffrin, D. J., Kiely, C. J. (1995) Adv. Mater. 7, 795-797 “Novel gold-dithiol nano-networks with nonmetallic electronic properties”, Janes, D, Kolaguta, L. V. R., Osifchin, R. G., Bielefeld, J. D., Andres, R. P., Henderson, J. I., Kubiak, C. P. (1995) Superlattices and Microstructures 18, 275-282 “Electronic conduction through 2D arrays of nanometer diameter metal clusters”, Brust, M., Bethell, D., Kiely, C. J., Schiffrin, D. J. (1998) Langmuir 14, 5425-5429 “Self-assembled gold nanoparticle thin films with non-metallic optical and electronic properties”).

The invention is now further illustrated by the accompanying figures and examples from which further embodiments, features and examples may be taken.

BRIEF DESCRIPTION OF THE DRAWINGS

FIG. 1: Schematic representations of possible bonding of dithiocarbamate compounds to gold surfaces. (a) Dithiocarbamate salt, purely electrostatic. (b) Dithiocarbamate salt, purely covalent. (c) Dithiocarbamate ester (deprotonated), purely electrostatic. (d) Dithiocarbamate ester, purely covalent.

All experimental examples provided in the following section were achieved by assembling dodecylamine stabilized Au-nanoparticles into films interconnected by various linker molecules using the layer-by-layer assembly technique and substrates with interdigitated electrode structures. The nanoparticles were synthesized according to a method described by Brust et al. (Brust, M., Bethell, D., Kiely, C. J., Schiffrin, D. J. (1998) Langmuir 14, 5425-5429 “Self-assembled gold nanoparticle thin films with nonmetallic optical and electronic properties”), using dodecylamine as a capping molecule. Prior to the assembly process, the electrodes were functionalized with a (3-aminopropyl)dimethylethoxysilane. For the assembly process, a 1 mM solution of the linker molecule was used and the concentration of the Au-nanoparticle solution was approx. 0.5 mM. The assembly process was monitored using UV-visible absorption spectroscopy. The film thickness for all assemblies was adjusted to an optical density (OD) of approximately 0.32-

0.35 at the maximum of the plasmon band, which amounts to a film thickness of roughly 30 nm as determined by AFM. The thickness of the films varies slightly from assembly to assembly. It has been verified, that these observed alterations in the film thickness introduce only a small uncertainty of ~5% in the I-V characteristics. With all assemblies, temperature dependent measurements of the conductivity were performed between ~100 K and ~300 K. The resistivity ρ of the assemblies were calculated according to $\rho=R\times A\times L^{-1}$, with A being the cross sectional area (A=30 nm×200 mm) and L=60 μm.

It has to be pointed out that the results obtained from these assemblies are for the following reasons average values for the multifunctional linker molecules:

The sizes of the Au-nanoparticles vary between approx. 3 and 30 nm.

The assembly of the nanoparticles was performed by the layer-by-layer assembly technique and as a result of the flexibility of the linker molecules the particle-particle distance can vary and the assembled films might contain some inhomogenieties.

Figure 2A:
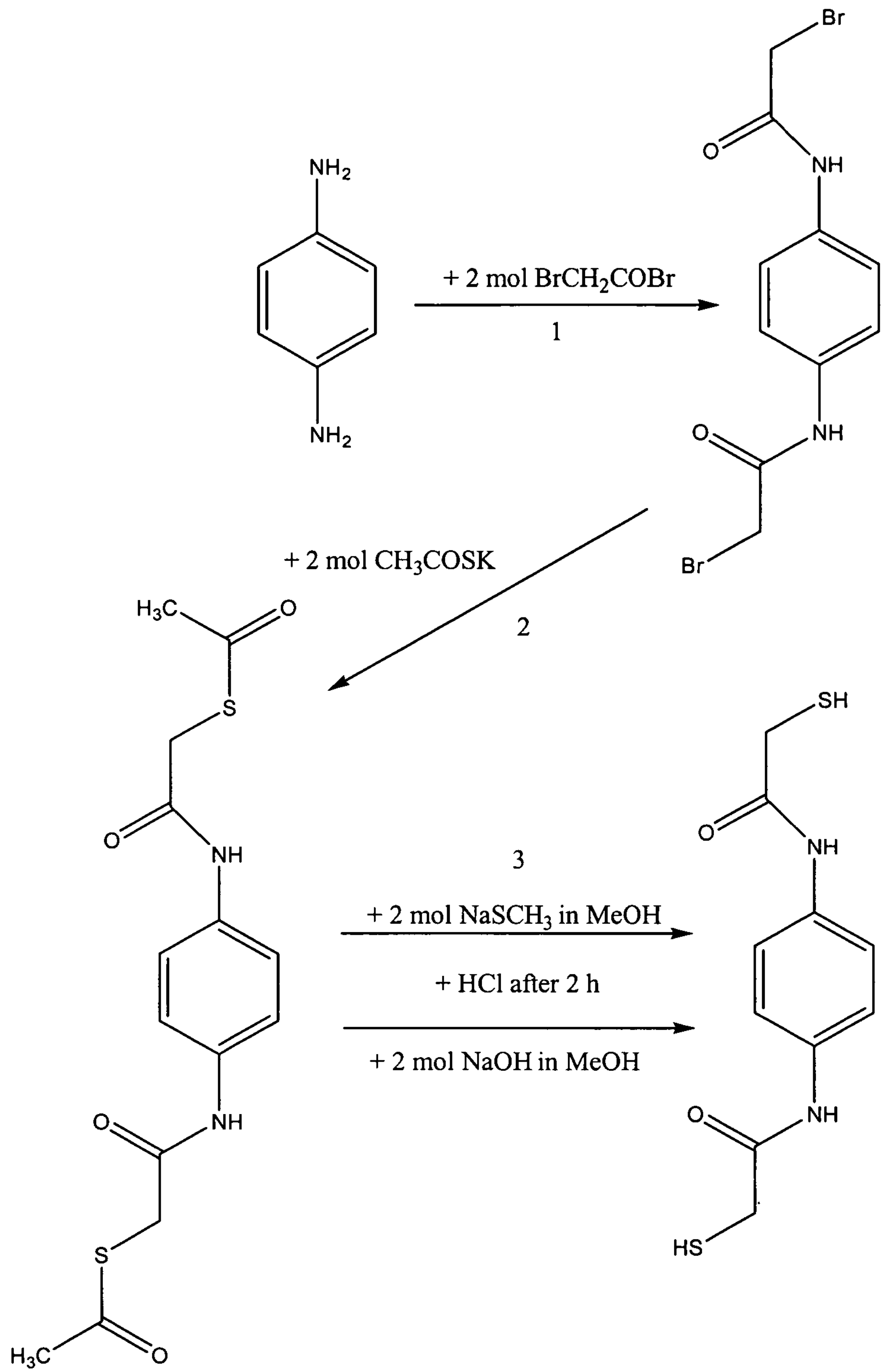
FIG. 2: Schematic drawing of the synthetic routes for substituting amino functionalized molecules with mercaptoacetamido groups (a) or with dithiocarbamates (b).
Figure 3:
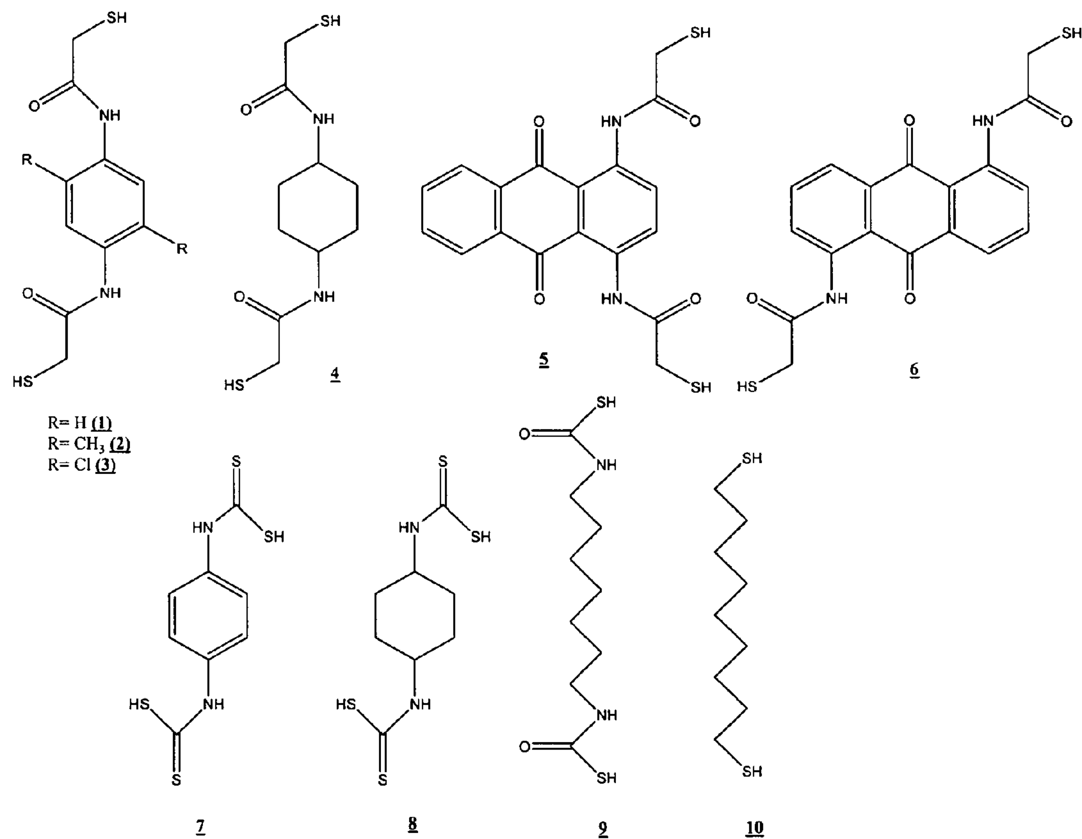
FIG. 3: Schematic drawing of the linker molecules synthesized according to the routes described in FIG. 2 (a and b). 1,4-dimercaptoacetamidobenzene (1), 1,4-dimercaptoacetamido-2,5-dimethylbenzene (2), 1,4-dimercaptoacetamido-2,5-dichlorobenzene (3), 1,4-dimercaptoacetamidocyclohexane (4), 1,4-dimercaptoacetamido-9,10-anthraquinone (5), 1,8-dimercaptoacetamido-9,10-anthraquinone (6), 1,4-dithiocarbamatobenzene disodium salt (7), 1,4-dithiocarbamatocyclohexane disodium salt (8) 1,8-dimercaptoacetamidoctane (9), and the commercially available 1,9-nonanedithiol (10).
Figure 4:
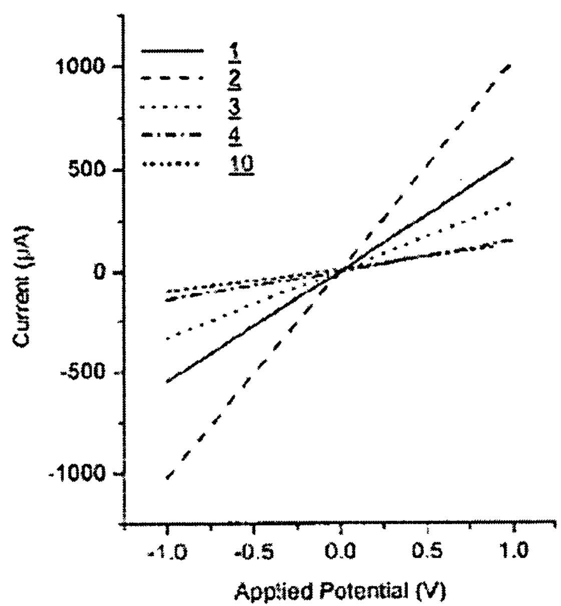
FIG. 4: I-V characteristics of Au-nanoparticles interconnected by the linker molecules 1 (-) 2 ( - - - ), 3( . . . ), 4 ( . - . - . ) and 10 ( - - - ) and self-assembled onto interdigitated Au-electrode structures by the layer-by-layer assembly technique to a film thickness of approx. 30 nm.
Figure 5:
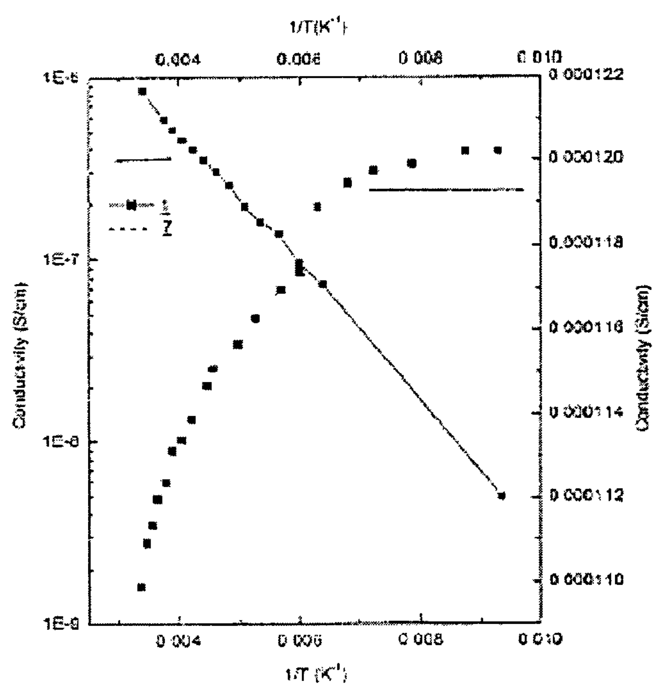
FIG. 5: Temperature dependence of the conductivity of Au-nanoparticles interconnected by the linker molecules 1 (-) and 7 ( - - - ) and self-assembled onto interdigitated Au-electrode structures by the layer-by-layer assembly technique to a film thickness of approx. 30 nm.

Phenylene-1,4-diamine derivatives with different substituents in the 2- and 5-positions of the conjugated π-system have been used to synthesize dithiol linker molecules (dimercaptoacetamido-benzene, R═H (1), R═$CH_3$ (2), and R═Cl (3)), depicted in FIG. 3. The change in the electron density on the ring structure itself can be described using the so-called Hammett parameter ($\sigma_p^+$). The Hammett equation for the calculation of substituent effects on reaction rates and chemical equilibria was introduced by Hammett using the ionization of meta- and para-substituted benzoic acids. From this equation the substituent constant $\sigma_p^+$ can be obtained which are negative for electron donating substituents and positive for electron accepting groups. These linker molecules were synthesized according to the route described in FIG. 2*a*. The I-V characteristics of the thin film assemblies using the three different dimercaptoacetamido-benzene derivatives provide evidence, that the substituents in positions 2 and 5 provides a means for fine tuning the conductivity through such assemblies (FIG. 4). The resistances obtained for these assemblies are summarized in Table 1. Temperature dependent measurements of the conductivity provide evidence for a thermal activated transport process (FIG. 5). The activation energy was obtained from fitting the plots σ ($T^{-1}$) to $$\sigma = \sigma_0 \cdot \exp\left(\frac{E_A}{k_B \cdot T}\right)$$

The activation energies obtained for these molecules are also summarized in Table 1.

TABLE 1

Summary of the resistivity ρ and the activation energy $E_A$ for the linker molecules 1-10 (see FIG. 3).

| Linker molecule | ρ (Ω cm) | $E_A$ (meV) |
|---|---|---|
| 1 | $18 \cdot 10^{1}$ | 74 |
| 2 | $10 \cdot 10^{1}$ | 110 |
| 3 | $3 \cdot 10^{2}$ | 96 |
| 4 | $6.9 \cdot 10^{2}$ | 88 |
| 5 | 6.41 | 31 |
| 6 | 6.0 | 112 |
| 7 | $9.1 \cdot 10^{-1}$ | — |
| 8 | $10.2 \cdot 10^{-1}$ | 25 |

TABLE 1-continued

Summary of the resistivity ρ and the activation energy $E_A$ for the linker molecules 1-10 (see FIG. 3).

| Linker molecule | ρ (Ω cm) | $E_A$ (meV) |
|---|---|---|
| 9 | $4.2 \cdot 10^{-1}$ | 15 |
| 10 | $8.7 \cdot 10^{2}$ | 42 |

Using the same synthetic route that was used for substituting the benzene derivatives (FIG. 3), diaminocyclohexane was used to synthesize a dimercaptoacetamido-cyelohexane (4) linker molecule. This system thus provides us with the possibility to directly obtain information to which degree the conductivity in these assemblies is reduced, when a conjugated system is exchanged with a non-conjugated system. The I-V characteristic of this linker molecule is also depicted in FIG. 4. The resistivity of the assembly obtained for this linker molecule is $\rho=69\times10^2$ Ωcm. This provides evidence that changing the degree of conjugation of the linker molecule influences the conductivity through these assemblies.

Figure 6:
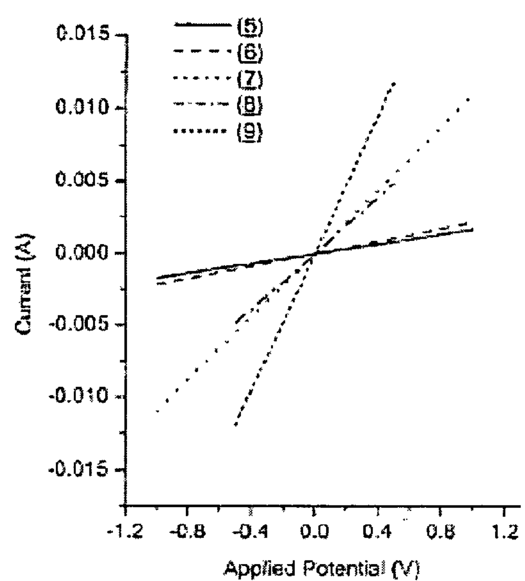
FIG. 6: I-V characteristics of Au-nanoparticles interconnected by the linker molecules 5 (-), 6 ( - - - ), 7 ( . . . ), 8 ( . - . - . ), and 9 ( - - - ) and self-assembled onto interdigitated Au electrode structures by the layer-by-layer assembly technique to a film thickness of approx. 30 nm.
Figure 7:
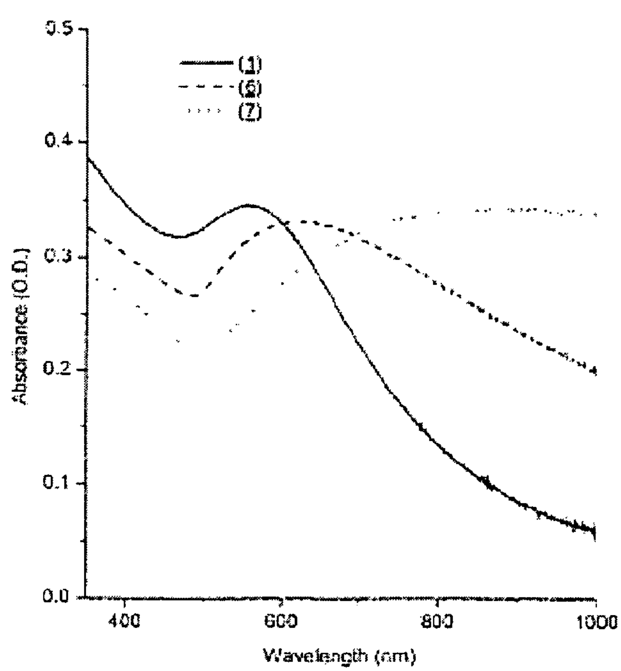
FIG. 7: UV-visible absorption spectra of Au-nanoparticles interconnected by linker molecules 1 (-), 6 ( - - - ), and 7 ( . . . ) assembled onto a silanized glass substrate by the layer-by-layer assembly technique to a film thickness of approx. 30 nm. The absorption spectra are due to two identical films, one on each side of the substrate.

The effect of introducing an electron acceptor as a linker molecule is demonstrated using 1,4-dimercaptoacetamido-anthraquinone (5) and 1,8-dimercaptoacetamido-anthraquinone (6). Both linker molecules were synthesized according to the route described in FIG. 2*a*. The room temperature resistivity of these assemblies was found to be 2 orders of magnitude smaller than the resistances obtained from assemblies interlinked with substituted diaminobenzene compounds. For both compounds 5 and 6, the resistance was of the same order of magnitude, ρ=6.41 Ωcm (5) and ρ=6.00 Ωcm (6), respectively. The I-V room temperature are shown in FIG. 6. These measurements show that introducing electron-accepting properties of linker molecules has a pronounced effect on the conductivity through the assembly. A pronounced difference between the assemblies of An nanoparticles interconnected with the anthraquinone derivative and the benzene derivatives is also evident in the absorption spectra of these molecules. In case of the linker molecules (1-4) the maximum of the plasmon absorption band peaked at ~550 nm, while in case of the anthraquinone linker molecules the maximum was red shifted to ~620 nm (FIG. 7). Since the dielectric vicinity of the particles is similar for all of the above-described assemblies this red shift could be an indication for a strong interaction between the nanoparticles induced by the linker molecule. These results show, that cross conjugation as described by Hush et al. (Hush, N. S., Reimers, J. R., Hall, L. E., Johnston, L. A., Crossley, M. J. (1998) Ann. New York Acad. Sci. 852, 1-21 "Optimization and chemical control of porphyrin-based molecular wires and switches") may not necessarily cause an attenuation of the coupling between the particles (vide supra). Hence considering the effect of cross-conjugation for tuning the conductivity in assemblies, the electron accepting properties have to be taken into consideration.

The molecular groups establishing the connection between the different nanostructured units, e.g. nanowires, nanoparticles, and possibly electrodes has a central function in the charge transport since the molecular design of this group is defining the type of bond that is formed between interconnected units. Included is also that the electrode or wire metal can be altered to alter the bonding group from the electrode/wire that participates in establishing the contact to the linker molecule depending on what type of tunnel barrier should be established for a specific interconnect.

Figure 2B:
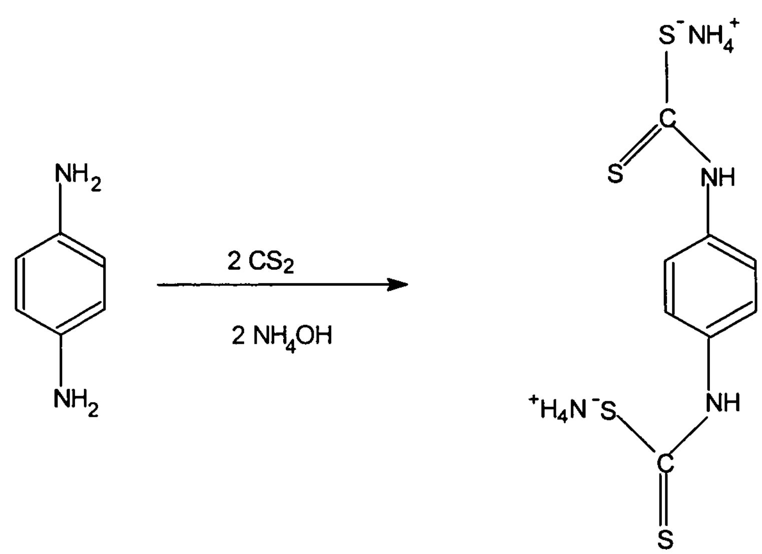

Two dithiocarbamate derivatives, 1,4-dithiocarbamato-benzene disodium salt (7) and 1,4-dithiocarbamatocyclohexane disodium salt (8), respectively, were synthesized according to the route described in FIG. 2*b*. Both bis-dithiocarbamate salts have the same central body X as the dithiols (1) and (4) in FIG. 3. The absorption characteristics of Au-nanoparticles interconnected with the 1,4-bis-dithiocarbamatobenzene (7) shows the typical characteristics of bulk gold (Kreibig, U., Genzel, L. (1985) Surf. Sci. 156, 678-700 "Optical absorption of small metallic particles"). Such absorption characteristics have been also observed using 2-mercaptoethanol for assembling Au-particles into films exhibiting a thickness of ~150 nm (Aguila, A., Murray, R. W. (2000) Langmuir 16, 5949-5954 "Monolayer-protected clusters with fluorescent dansyl ligands"). In contrast, the assembly using the 1,4-dithiocarbamato-cyclohexane (8) exhibits absorption characteristics similar to the ones observed for the anthraquinone-substituted linker molecules. The plasmon band peaks at ~620 nm and there is an increase in absorption in the near infrared. Temperature dependent studies of the dithiocarbamate assembly show typical metal behavior, i.e. with decreasing temperature an increase in the conductivity could be observed (FIG. 5). The I-V characteristics at room temperatures are shown in FIG. 6. The resistivities obtained for substances 7 and 8 are $9.1\times10^{-1}$ Ωcm and $10.2\times10^{-1}$ Ωcm, respectively. The corresponding value for bulk gold at 20° C. is $\rho=2.4\times10^{-4}$ Ωcm (Weast, R. G. (Edt.) (1988) "CRC Handbook of Chemistry and Physics", $69^{th}$ Ed.). Similar resistivities have also been achieved by using a very short linker molecule, 2-mercaptoethanol, and by increasing the film thickness (Aguila, A. Murray, R. W. (2000), Langmuir, 16, 5949-5954 "Monolayer-protected clusters with fluorescent dansyl ligands"). These measurements provide evidence that the binding of linker molecules to the particle has a significant effect on the room temperature resistance of these assemblies, as it has been suggested by the theoretical calculations of Emberly and Kirczenow (Emberly, E. G., Kirczenow, G. (1998) Ann. New York Acad. Sci. 852, 1-21 "Theory of electrical conductance through a molecule").

1,8-Dimercaptoacetamidooctane (9) (FIG. 3) was also used for interconnecting Au-nanoparticles into thin films. This molecule was synthesized for comparison of the I-V characteristics obtained from the commercially available 1,9-nonanedithiol (10), which has been studied in detailed in the literature. In the case of (10), the resistivity of the assembly is $\rho=8.7\times10^{2}$ Ωcm, whereas in the case of the amide substituted linker molecule (9) $\rho=4.2\times10^{-1}$ Ωcm. Thus, although both linker molecules are of comparable length, the resistivities vary by three orders of magnitude. This result indicates that hydrogen-bond network between the amide groups can influence the charge transport, leading to a considerable enhancement of conductivity, although the linker molecules are quite flexible and it is also possible that the distances between the particles may be different in the two kinds of assemblies.

This invention extends the class of molecules to be used in the referred assembly process to polyfunctional dithiocarbamate esters, in particular bis-dithiocarbamate esters, which can be used for the assembly of molecule interlinked metal-nanoparticle composites. To the knowledge of the inventors, there is no report on the use of polyfunctional dithiocarbamate esters for the preparation of the said assemblies. Dithiocarbamate esters may be used instead of the dithiocarbamates as interlinking molecules without any restriction. It has been observed that the said assembly process can be performed in the same manner as it is performed with any other dithiol or dithiocarbamate salt.

Figure 8:
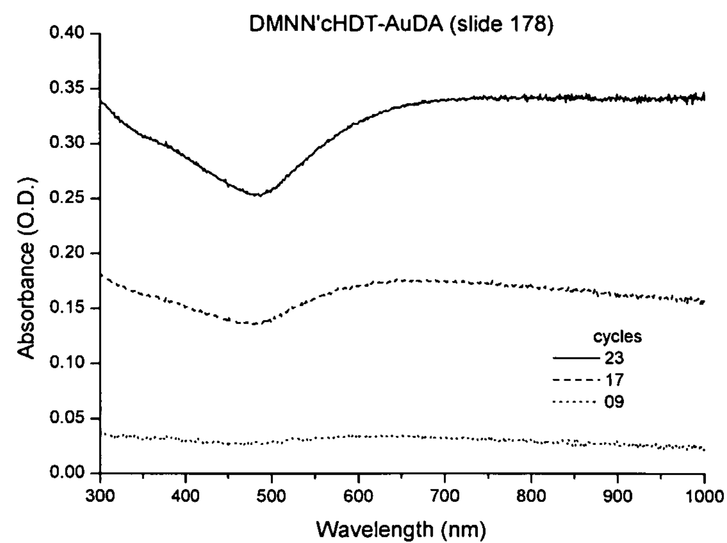
FIG. 8: UV-visible absorption spectra of films of Au-nanoparticles interconnected by the linker molecule dimethyl-N,N'-1,4-diaminocyclohexane-bis(dithiocarbamate) (11) assembled onto a silanized glass substrate by the layer-by-layer assembly technique. The thickness of the film after cycle 23 is approx. 20 nm. The absorption spectra are due to two identical films, one on each side of the substrate.
Figure 9:
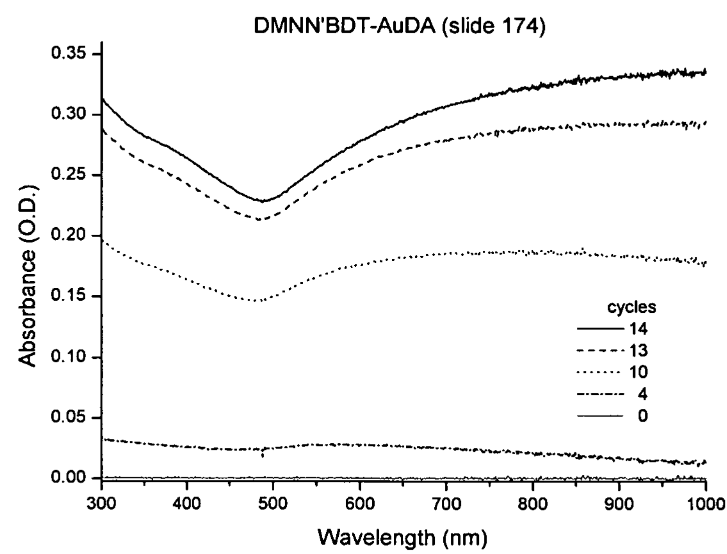
FIG. 9: UV-visible absorption spectra of films of Au-nanoparticles interconnected by the linker molecule dim ethyl-N,N'-1,4-diaminobenzene-bis(dithiocarbamate) (12) assembled onto a silanized glass substrate by the layer-by-layer assembly technique. The thickness of the film after cycle 14 is approx. 15 nm. The absorption spectra are due to two identical films, one on each side of the substrate.
Figure 10:
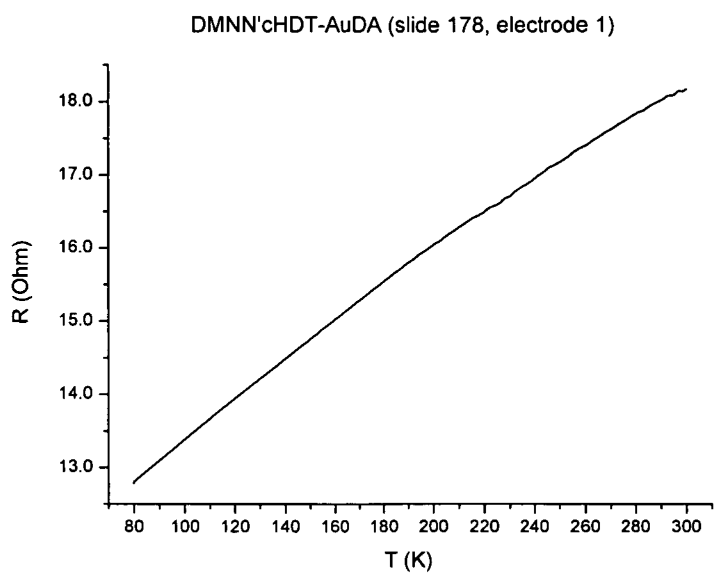
FIG. 10: Temperature dependence of the resistivity of Au-nanoparticles interconnected by the linker molecule dimethyl-N,N'-1,4-diaminocyclohexane-bis(dithiocarbamate) (11) and self-assembled onto interdigitated Au-electrode structures by the layer-by-layer assembly technique to a film thickness of approx. 20 nm.
Figure 11:
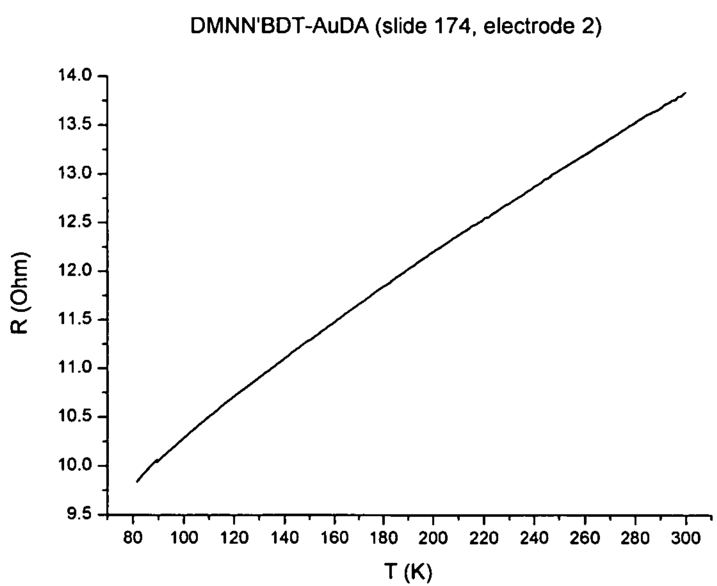
FIG. 11: Temperature dependence of the resistivity of Au-nanoparticles interconnected by the linker molecule dimethyl-N,N'-1,4-diaminobenzene-bis(dithiocarbamate) ( 12) and self-assembled onto interdigitated Au-electrode structures by the layer-by-layer assembly technique to a film thickness of approx. 15 nm.

The UV-visible spectra measured during the assembly of gold nanoparticle films interlinked with dithiocarbamate esters, dimethyl-N,N'-1,4-cyclohexylamine-bis(dithiocarbamate) (11) and dimethyl-N,N'-1,4-diaminobenzene-bis (dithiocarbamate) (12), are shown in FIG. 8 and FIG. 9, respectively. The spectra in both cases resemble gold films, indicating metallic characteristics of the films. Plots of the temperature dependence of the resistivity further demonstrate the metallic electrical characteristics of the films, since the resistivity decreases with decreasing temperature in films of gold nanoparticles interlinked with both 11 (FIG. 10) and 12 (FIG. 11).

A detailed explanation of the optical and electrical characteristics of the corresponding assemblies prepared with dithiocarbamate salts is given by Wessels et al. (Wessels, J. M., Nothofer, H.-G., Ford, W. E., von Wrochem, F., Scholz, F., Vossmeyer, T., Schroedter, A., Weller, H., Yasuda, A. (2004) J. Am. Chem. Sec. 126, 3349-3356, "Optical and electrical properties of three-dimensional interlinked gold nanoparticle assemblies"). In brief, these finding indicate that by using dithiocarbamate esters having either aliphatic or conjugated core X it is possible to tune the conductivity through such organic-inorganic composites from insulating to metallic behavior.

The invention claimed is:

1. A nanoparticle-linker assembly comprising:

at least two nanoparticle units; and a multifunctional linker molecule;

wherein the at least two nanoparticle units are at least two units selected from the group consisting of a nanowire, a nanotube, and a nanobelt, the multifunctional linker molecule is bound to each of the at least two nanoparticle units, and the multifunctional linker molecule is of the structure

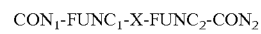

$CON_1\text{-}FUNC_1\text{-}X\text{-}FUNC_2\text{-}CON_2$ wherein

X is a central body of the molecule which comprises one selected from the group consisting of an alkane, an alkene of 3 to 12 carbon atoms, an alkyne, and an aromatic π-system, $FUNC_1$ and $FUNC_2$ independently of each other are molecular groups which are not hydrocarbon groups and which provide to the multifunctional linker molecule a capability of forming intermolecular and/or intramolecular hydrogen bonding networks, and $CON_1$ and $CON_2$ independently of each other are molecular groups which bind to the at least two nanoparticle units.

2. The nanoparticle-linker assembly according to claim 1, wherein $CON_1$ and $CON_2$ are identical or different and $FUNC_1$ and $FUNC_2$ are identical or different.

3. The nanoparticle-linker assembly according to claim 1, wherein a length of the multifunctional linker molecule is between about 8 Å and about 30 Å.

4. The nanoparticle-linker assembly according to claim 1, wherein a structure of X comprises a hydrocarbon skeleton with two identical or different substituents that connect to or form the molecular groups $FUNC_1$ and $FUNC_2$.

5. The nanoparticle-linker assembly according to claim 4, wherein X comprises two substituents selected from the group consisting of an amine, a carboxylic acid, a sulfonic acid and a phosphonic acid.

6. The nanoparticle-linker assembly according to claim 4, wherein the substituents of X are directed at an angle α relative to one another such that $90°<\alpha<270°$.

7. The nanoparticle-linker assembly according to claim 4, wherein

X comprises at least one structural component selected from the group consisting of:

a conjugated system, an aromatic π-system; a heteroatom selected from the group consisting of N, O and S; an electron donating substituent selected from the group consisting of $CH_3$, $O^-$, $COO^-$, $N(CH_3)_2$ and $NH_2$; and an electron accepting substituent selected from the group consisting of CN, $COCH_3$, $CONH_2$, $CO_2CH_3$, $N(CH_3)_3^+$, $NO_2$, F, Cl, Br, I, $OCF_3$, and $SO_2NH_2$.

8. The nanoparticle-linker assembly according to claim 4, wherein X is a structure selected from the group consisting of:

a structure having a formula selected from the group of formulae consisting of:

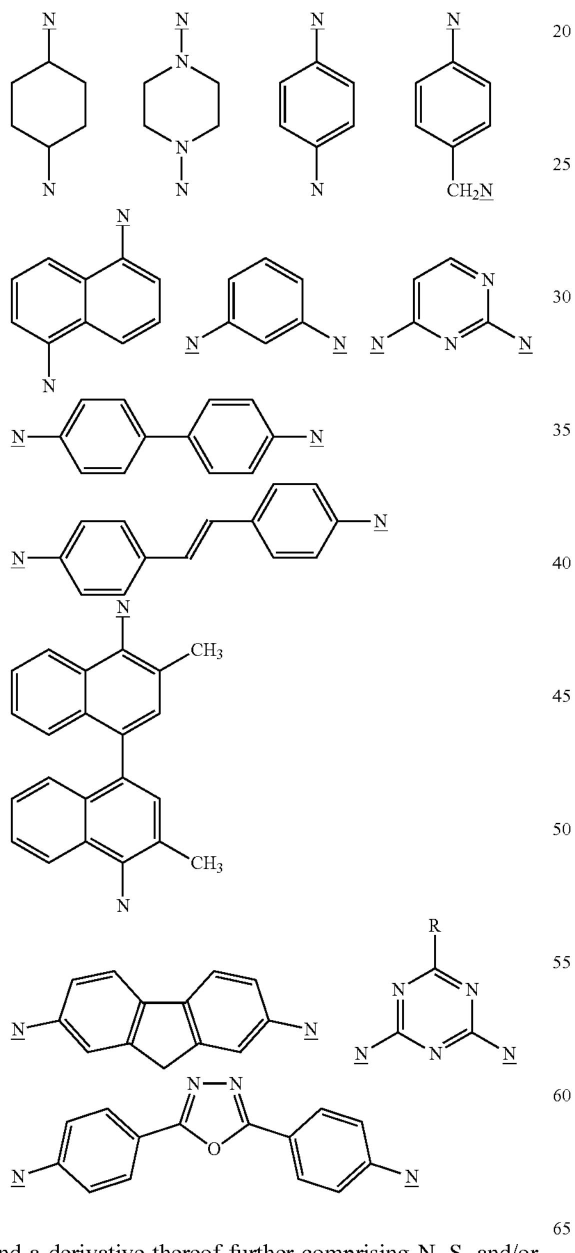

and a derivative thereof further comprising N, S, and/or O, or electron donating or accepting substituents;

wherein R is methyl, phenyl or alkoxyl and wherein $FUNC_1$ and $FUNC_2$ are attached via the N-atoms of the two amine substituents indicated by N;

a structure having a formula selected from the group of formulae consisting of:

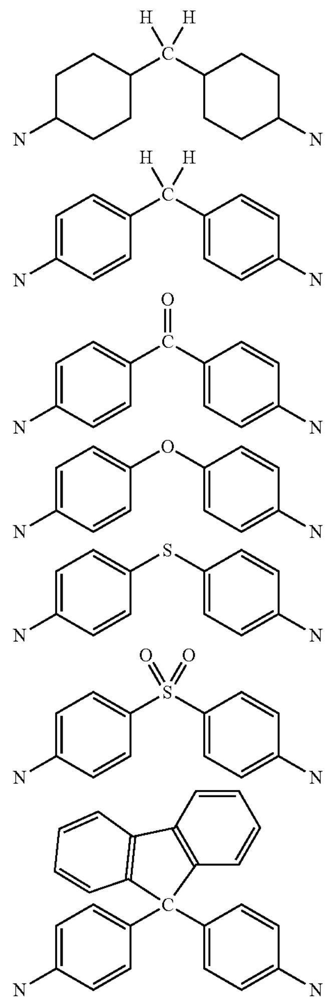

and derivatives thereof containing electron donating or accepting substituents wherein $FUNC_1$ and $FUNC_2$ are attached via the N-atoms of the amine substituents indicated by N;

a structure having a formula selected from the group of formulae consisting of:

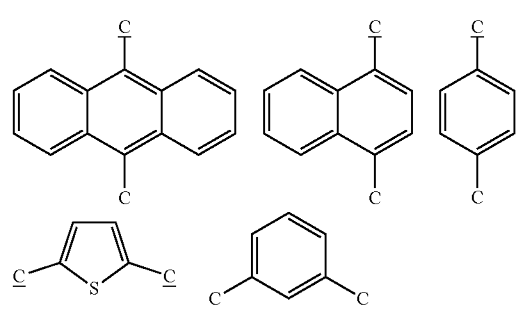

-continued

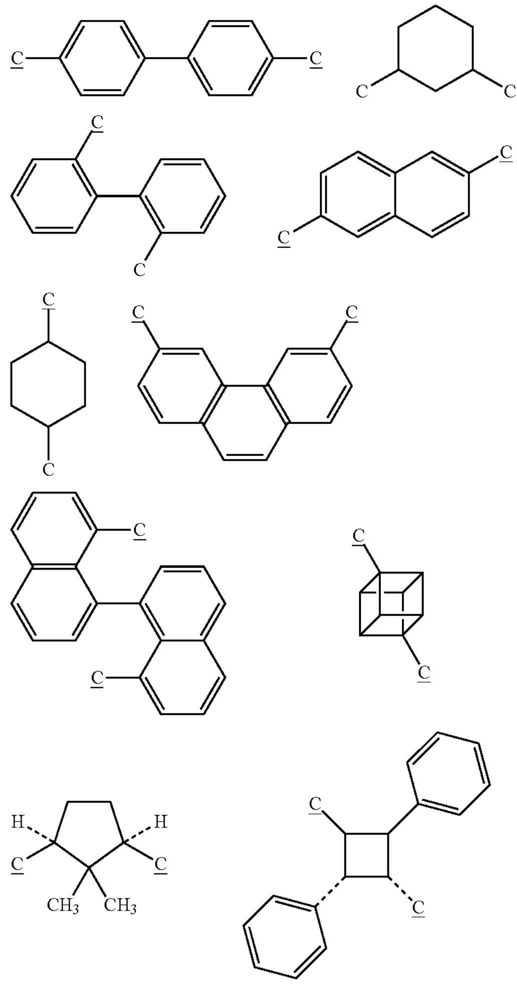

and derivatives thereof comprising N, S, and/or O, or electron donating or accepting substituents; and wherein $FUNC_1$ and $FUNC_2$ are attached via the carbon atoms of the two carboxylic acid substituents indicated by C;

a structure having a formula selected from the group of formulae consisting of:

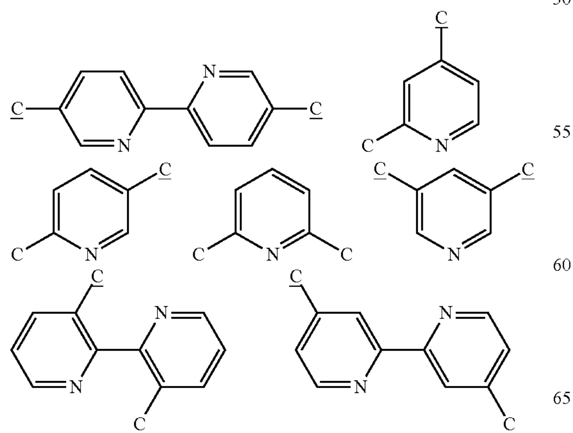

-continued

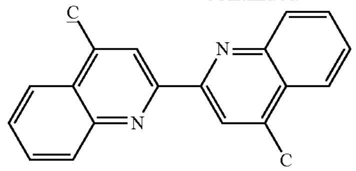

wherein $FUNC_1$ and $FUNC_2$ are attached via the carbon atoms of the two carboxylic acid substituents indicated by C;

a structure having a formula selected from the group of formulae consisting of:

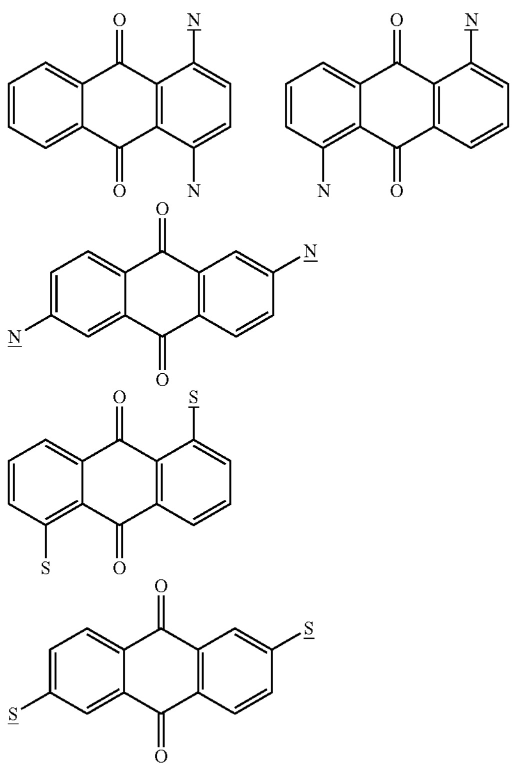

and derivatives thereof containing electron donating or accepting substituents wherein $FUNC_1$ and $FUNC_2$ are attached via the N- or S-atoms of the two amine or sulfonic acid substituents indicated by N and S;

a structure having a formula selected from e group of formulae consisting of:

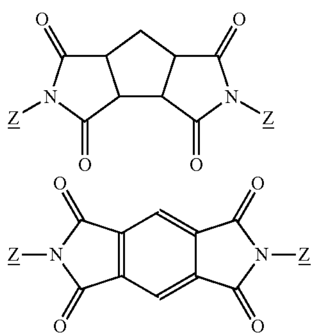

-continued

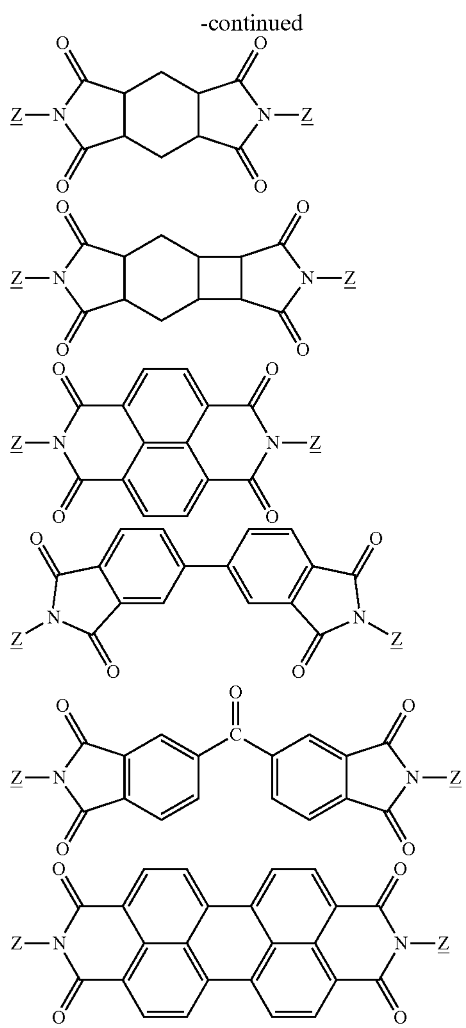

wherein Z represents amine (Z=N) or a carboxymethyl (Z=CH(R)C) residue, wherein R is an amino acid side chain and $FUNC_1$ and $FUNC_2$ are attached via Z; and c) an electron donor selected from hydroquinones substituted with at least two groups selected from the groups consisting of an amine, a carboxylic acid, a sulfonic acid and a phosphonic acid; and d) an electron acceptor selected from quinones and diimides substituted with at least two groups selected from the groups consisting of an amine, a carboxylic acid, a sulfonic acid and a phosphonic acid.

9. The nanoparticle-linker assembly according to claim 8, wherein $FUNC_1$ and $FUNC_2$ independently of each other are connected to X via N, C, S, or P, and are selected from the group consisting of:

—NH, —NHCO, —NHCONH, —NHCSNH, —NHCONHNH, —NHCSNHNH, —NHCONHNHCO, and —NHCONHNHCO in case of a connection via N;

—CONH, —CONHNH, and —CONHNHCO in case of a connection via C;

—$SO_2NH$, —$SO_2NHNH$, and —$SO_2NHNHCO$ in case of a connection via S; and

—$PO_2NH$, —$PO_2NHNH$, and —$PO_2NHNHCO$ in case of a connection via P.

10. The nanoparticle-linker assembly according to claim 9, wherein CON $_1$ and CON $_2$ connected to $FUNC_1$ and $FUNC_2$ via NH or CO, independently of each other are selected from the groups consisting of:

—$(CHR)_nCOOH$; —$(CHR)_nNC$; —$(CHR)_nNH_2$; —$(CHR)_nNHCS_2H$; —$(CHR)_nOPO_3H_2$; —$(CHR)_nOSO_3H$; —$(CHR)_nPO_3H_2$; —$(CHR)_nSH$; —$(CHR)_nSO_3H$; —CSOH; and —$CS_2H$ in case of a connection via NH; and —$(CHR)_nCOOH$; —$(CHR)_nNC$; —$(CHR)_nNH_2$; —$(CHR)_nNHCS_2H$; —$(CHR)_nOPO_3H_2$; —$(CHR)_nOSO_3H$; —$(CHR)_nPO_3H_2$; —$(CHR)_nSH$; and —$(CHR)_nSO_3H$ in case of a connection via CO; and ionic forms thereof, wherein R is H, $CH_2OH$, or $CH_3$ and n is 1 or 2.

11. The nanoparticle-linker assembly according to claim 10, wherein CON $_1$ and CON $_2$ independently of each other comprise branched molecular structures.

12. The nanoparticle-linker assembly according to claim 10, wherein CON $_1$ and CON $_2$ independently of each other comprise dithiocarbarnateesters or bis-dithiocarbamateesters.

13. The nanoparticle-linker assembly according to claim 1, wherein the multifunctional linker molecule is one selected from the group consisting of 1,4-dimercaptoacetamidobenzene of the formulae:

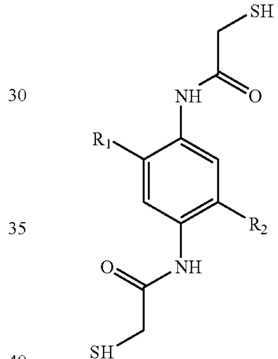

wherein $R_{1,2}$ is independently selected from $CH_3$ and/or Cl; 1,4-dimercaptoacetamidocyclohexane, 1,4-dimercaptoacetamido-9,10-anthraquinone, 1,5-dimercaptoacetamido-9,10-anthraquinone, 1,8-dimercaptoacetamidooctane, 1,4-dithiocarbamatobenzene, 1,4-dithiocarbamatocyclohexane, dimethyl-N,N'-1,4-cyclohexylaminebis(dithiocarbamate), and dimethyl-N,N'-1,4-phenyleneaminebis(dithiocarbamate).

14. A 1-, 2-, or 3-dimensional assembly of nanostructured units comprising the nanoparticle-linker assembly according to claim 1, wherein the conductivity of the assembly is determined by the structure of the multifunctional linker.

15. The 1-, 2-, or 3-dimensional assembly of nanostructured units according to claim 14, wherein the nanoparticle units comprise gold.

16. A film comprising the 1-, or 3-dimensional assembly of nanostructured units according to claim 14.

17. An electronic circuit element, electrode or metal coating comprising the 1-, 2-, or 3-dimensional assembly of nanostructured units according to claim 14 wherein the circuit element, electrode or metal coating is self-assembled.

18. A film comprising the 1-, 2-, or 3-dimensional assembly of nanostructured units according to claim 15.

19. An electronic circuit element, electrode or metal coating comprising the 1-, 2- or 3-dimensional assembly of nanostructured units according to claim 15, wherein the circuit element, electrode or metal coating is self-assembled.

20. The 1-, 2- or 3-dimensional assembly of nanostructured units according to claim 15, wherein a size of a gold nanoparticles in the nanoparucle unit is from about 5 nm to about 20 nm, a resistivity of the assembly is of the order of $10^{-2}$ Ωcm for a film thickness of about 30 nm, and the resistivity decreases with decreasing temperature.

* * * * *